United States Patent
Ashkenazi et al.

(10) Patent No.: US 6,252,050 B1
(45) Date of Patent: Jun. 26, 2001

(54) METHOD FOR MAKING MONOCLONAL ANTIBODIES AND CROSS-REACTIVE ANTIBODIES OBTAINABLE BY THE METHOD

(75) Inventors: Avi J. Ashkenazi, San Mateo; Anan Chuntharapai, Colma; K. Jin Kim, Los Altos, all of CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 09/329,633

(22) Filed: Jun. 10, 1999

Related U.S. Application Data

(60) Provisional application No. 60/089,253, filed on Jun. 12, 1998.

(51) Int. Cl.[7] .................. A61K 39/395; C07K 16/28
(52) U.S. Cl. ..................... 530/387.3; 424/143.1; 424/174.1; 435/334; 436/548; 530/388.15; 530/388.22; 530/389.1
(58) Field of Search .............. 435/334; 436/548; 530/387.3, 388.15, 388.22, 389.1; 424/143.1, 174.1

(56) References Cited

U.S. PATENT DOCUMENTS

| | | |
|---|---|---|
| 4,816,567 | 3/1989 | Cabilly et al. . |
| 4,855,235 | 8/1989 | Takahashi et al. . |
| 5,071,759 | * 12/1991 | Rothman et al. ............ 436/548 |
| 5,153,118 | 10/1992 | Wright, Jr. et al. . |
| 5,158,885 | 10/1992 | Bradstock et al. . |
| 5,622,701 | * 4/1997 | Berg .......................... 435/334 |
| 6,030,945 | * 2/2000 | Ashkenazi .................. 514/12 |
| 6,072,047 | * 6/2000 | Rauch et al. ............... 536/23.5 |

FOREIGN PATENT DOCUMENTS

| | | |
|---|---|---|
| WO 91/02805 | 3/1991 | (WO) . |
| WO 93/22343 | 11/1993 | (WO) . |
| 9705170 | * 2/1997 | (WO) . |
| WO 97/25428 | 7/1997 | (WO) . |
| 9903992 | * 1/1999 | (WO) . |
| 9909165 | * 2/1999 | (WO) . |
| 9964461 | * 12/1999 | (WO) . |

OTHER PUBLICATIONS

Ashkenazi et al., "Protection Against Endotoxic Shock by a Tumor Necrosis Factor Receptor Immunoadhesin" *Proc. Natl. Acad. Sci.* 88:10535–10539 (1991).

Chuntharapai and Kim, "Generation of Monoclonal Antibodies to Chemokine Receptors" *Methods in Enzymology* 288:15–27 (1997).

Emery et al., "Osteoprotegerin Is a Receptor for the Cytotoxic Ligand Trail" *Journal of Interferon and Cytokine Research* (Abstract No. 2.17 from the 7th Intl. Tumor Necrosis Factor Congress May 17–21) 18(5):A–47 (May 1998).

Fishwild et al., "High-avidity human IgGκ monoclonal antibodies from a novel strain of minilocus transgenic mice" *Nature Biotechnology* 14(7):845–851 (Jul. 1996).

(List continued on next page.)

*Primary Examiner*—David Saunders
(74) *Attorney, Agent, or Firm*—Wendy M. Lee

(57) ABSTRACT

A method of making monoclonal antibodies according to a mixed antigen immunization protocol is described. In addition, antibodies obtainable by the method are disclosed which specifically cross-react with two or more different receptors to which Apo-2 ligand (Apo-2L) can bind.

19 Claims, 8 Drawing Sheets

OTHER PUBLICATIONS

Glassy, M., "Production methods for generating human monoclonal antibodies" *Human Antibodies & Hybridomas* 4(4):154–165 (Oct. 1993).

Hoogenboom and Winter, "By-passing immunisation: human antibodies from synthetic repertoires of germline $V_H$ gene segments rearranged in vitro" *J. Mol. Biol.* 227:381–388 (1992).

Jones et al., "Replacing the Complementarity–determining Regions in a Human Antibody with Those From a Mouse" *Nature* 321:522–525 (May 29, 1986).

Kohler et al., "Continuous Cultures of Fused Cells Secreting Antibody of Predefined Specificity" *Nature* 256:495–497 (Aug. 7, 1975).

Marks et al., "By-passing immunization: human antibodies from V–gene libraries displayed on phage" *J. Mol. Biol.* 222:581–597 (1991).

Marsters et al., "A Novel Receptor for Apo2L/Trail Contains a Truncated Death Domain" *Current Biology* 7:1003–1006 (1997).

Mendez et al., "Functional transplant of megabase human immunoglobulin loci recapitulates human antibody response in mice" *Nature Genetics* 15:146–156 (Feb. 1997).

Olsson and Kaplan, "Human–human hybridomas producing monoclonal antibodies of predefined antigenic specificity" *Proc. Natl. Acad. Sci. USA* 77(9):5429–5431 (1980).

Pan et al., "The Receptor for the Cytotoxic Ligand Trail" *Science* 276:111–113 (1997).

Peterson, N., "Recombinant antibodies: alternative strategies for developing and manipulating murine–derived monoclonal antibodies" *Laboratory Animal Science* 46(1):8–14 (Feb. 1996).

Pitti et al., "Induction of Apoptosis by Apo-2 Ligand, a New Member of the Tumor Necrosis Factor Cytokine Family" *Journal of Biological Chemistry* 271:12687–12690 (1996).

Riechmann et al., "Reshaping Human Antibodies for Therapy" *Nature* 332:323–327 (Mar. 24, 1988).

Sheridan et al., "Control of Trail–Induced Apoptosis by a Family of Signaling and Decoy Receptors" *Science* 277:818–821 (1997).

Simonet et al., "Osteoprotegerin: A Novel Secreted Protein Involved in the Regulation of Bone Density" *Cell* 89:309–319 (Apr. 18, 1997).

Steinitz et al., "EB virus–induced B lymphocyte Cell lines producing specific antibody" *Nature* 269(5627):420–422 (Sep. 29, 1977).

Vaughan et al., "Human Antibodies With Sub–nanomolar Affinities Isolated From a Large Non–immunized Phage Display Library" *Nature Biotechnology* 14:309–314 (1996).

Verhoeyen et al., "Reshaping Human Antibodies: Grafting an Antilysozyme Activity" *Science* 239:1534–1536 (Mar. 25, 1988).

Ellis, S., "Recognition of HLA–B27 and Related Antigen by a Monoclonal Antibody" *Human Immunology* 5:49–59 (1982).

Jolliffe, L., "Humanized antibodies: enhancing therapeutic utility through antibody engineering" *International Reviews of Immunology* 10(2–3):241–250 (1993).

Mehta et al., "Simultaneous production of antibodies against $T_3$ and $T_4$ in a single animal; their characteristics and usefulness in radioimmunoassay" *International Journal of Radiation Applications & Instrumentation—Part B, Nuclear Medicine & Biology* 16(6):599–601 (1989).

Milstein, C., "The Wellcome Foundation Lecture, 1980: monoclonal antibodies from hybrid myelomas" *Proceedings of the Royal Society of London—Series B: Biological Sciences* 211(1185):393–412 (Mar. 27, 1981).

* cited by examiner

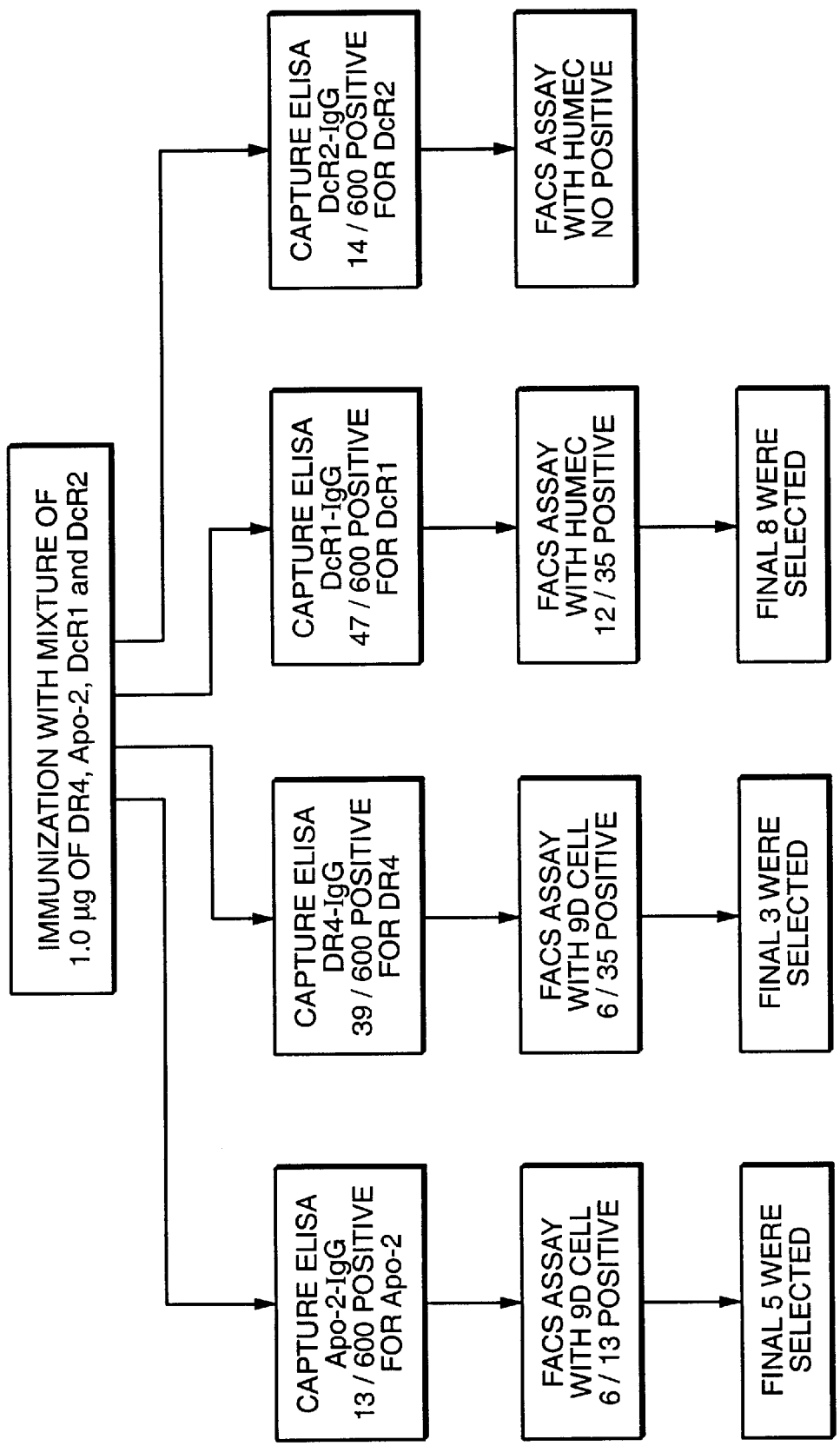
FIG._1

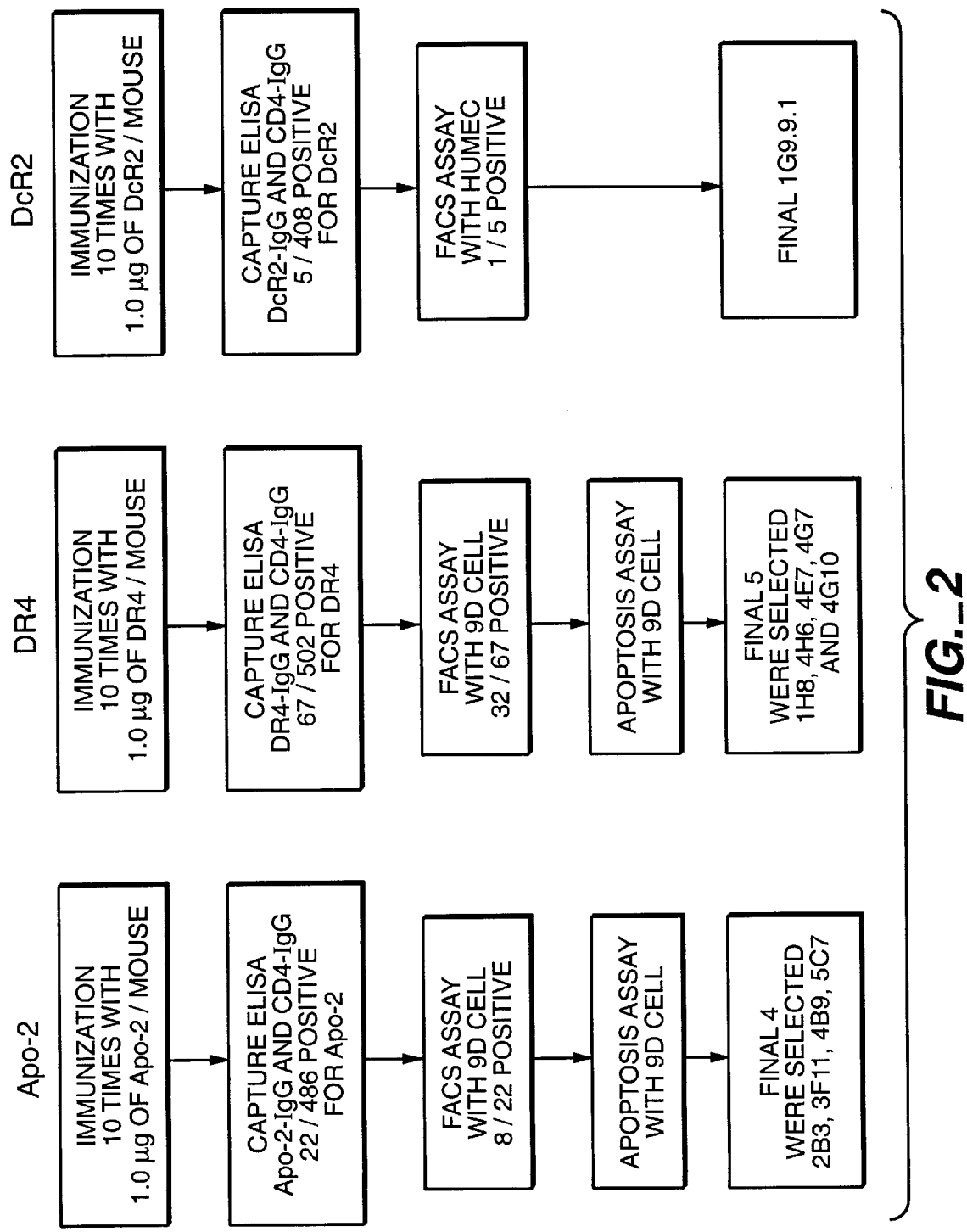
FIG._2

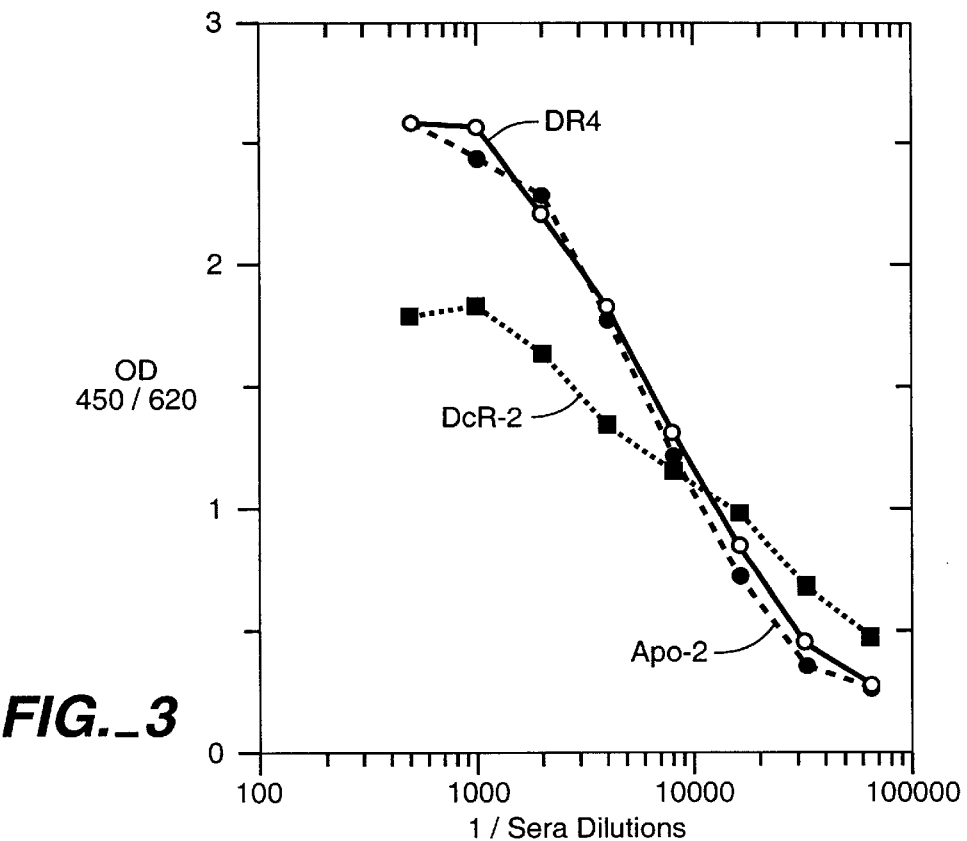
FIG._3
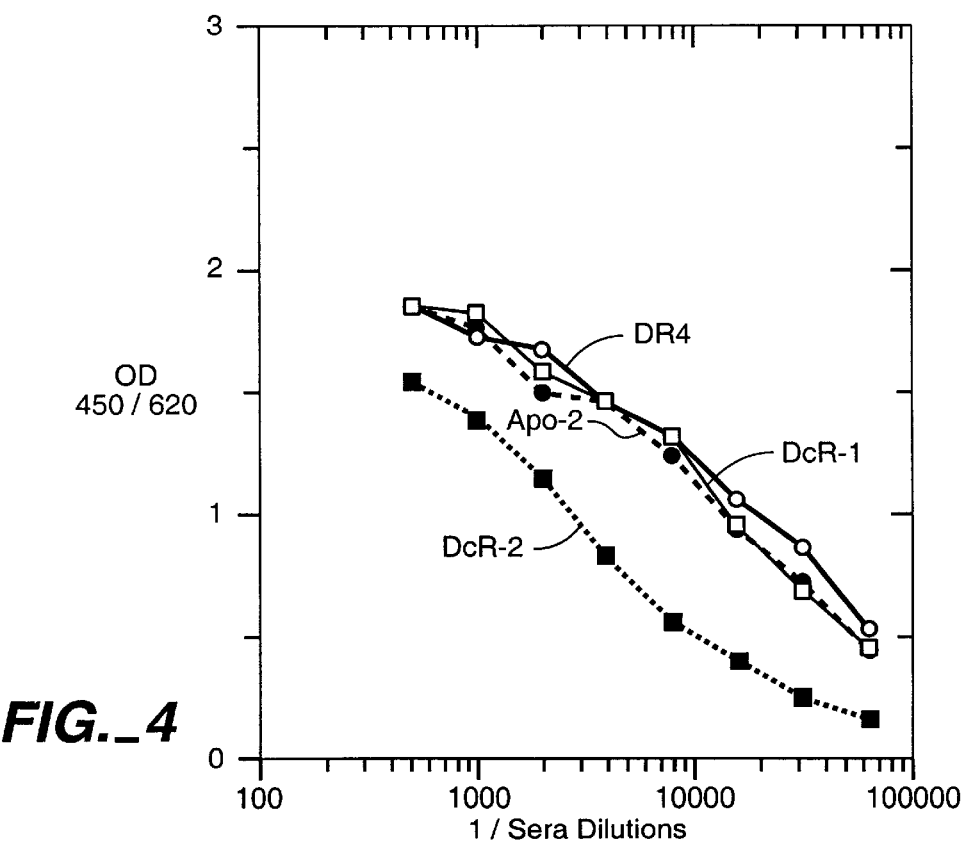
FIG._4

```
  1 CCCACGCGTC CGATAAATC AGCACGCGGC CGGAGAACCC CGAATCTCT GCGCCCACAA AATACACCGA CGATGCCCGA TCTACTTTAA GGGCTGAAAC
    GGGTGCGCAG GCGTATTTAG TCGTGCGCCG GCCTCTTGGG GCGTTAGAGA CGCGGGTGTT TTATGTGGCT GCTACGGGCT AGATGAAATT CCCGACTTTG

101 CCACGGGCCT GAGAGACTAT AAGAGCGTTC CCTACCGCCA TGGAACAACG GGGACAGAAC GCCCCGGCCG CTTCGGGGGC CCGGAAAAGG CACGGCCCAG
    GGTGCCCCGA CTCTCTGATA TTCTCGCAAG GGATGGCGGT ACCTTGTTGC CCCTGTCTTG CGGGGCCGGC GAAGCCCCCG GGCCTTTTCC GTGCCGGGTC
  1                                           M  etGluGlnAr gGlyGlnAsn AlaProAlaA laSerGlyAl aArgLysArg HisGlyProGly

201 GACCCAGGGA GGCGCGGGGA GCCAGGCCTG GGCTCCGGGT CCCAAGACC CTTGTGCTCG TTGTCGCCGC GGTCCTGCTG TTGGTCTCAG CTGAGTCTGC
    CTGGGTCCCT CCGCGCCCCT CGGTCCGGAC CCGAGGCCCA GGGTTCTGG GAACACGAGC AACAGCGGCG CCAGGACGAC AACCAGAGTC GACTCAGACG
 22 ProArgGl uAlaArgGly AlaArgProG lyLeuArgVa lProLysThr LeuValLeuV alValAlaAl aValLeuLeu LeuValSerA laGluSerAla

301 TCTGATCACC CAACAAGACC TAGCTCCCCA GCAGAGAGCG GCCCCACAAC AAAAGAGGTC CAGCCCCTCA GAGGATTGT GTCCACCTGG ACACCATATC
    AGACTAGTGG GTTGTTCTGG ATCGAGGGGT CGTCTCTCGC CGGGGTGTTG TTTTCTCCAG GTCGGGGAGT CTCCCTAACA CAGGTGGACC TGTGGTATAG
 55 LeuIleThr GlnGlnAspL euAlaProGl nGlnArgAla AlaProGlnG lnLysArgSe rSerProSer GluGlyLeuC ysProProGl yHisHisIle

401 TCAGAAGACG GTAGAGATTG CATCTCCTGC AAATATGGAC AGGACTATAG CACTCACTGG AATGACCTCC TTTTCTGCTT GCGCTGCACC AGTGTGATT
    AGTCTTCTGC CATCTCTAAC GTAGAGGACG TTTATACCTG TCCTGATATC GTGAGTGACC TTACTGGAGG AAAAGACGAA CGCGACGTGG TCCACACTAA
 88 SerGluAspG lyArgAspCy sIleSerCys LysTyrGlyG lnAspTyrSe rThrHisTrp AsnAspLeuL euPheCysLe uArgCysThr ArgCysAspSer

501 CAGGTGAAGT GGAGCTAAGT CCCTGCACCA CGACCAGAAA CAGTGCGAAG AAGGCACCTT CCGGGAAGAA GATTCCCTG AGATGTGCCG
    GTCCACTTCA CCTCGATTCA GGGACGTGGT GCTGGTCTTT GTCACGCTTC TTCCGTGGAA GGCCCTTCTT CTAAGAGGAC TCTACACGGC
122 GlyGluVa lGluLeuSer ProCysThrT hrThrArgAs nThrValCys GlnCysGluG luGlyThrPh eArgGluGlu AspSerProG luMetCysArg

601 GAAGTGCCGC ACAGGGTGTC CCAGAGGGAT GGTCAAGGTC CAGGACCTT CACCCTGAG TGTGTCCACA AGAATCAGG CCTGAAAGGC ATCTGCTCAG
    CTTCACGGCG TGTCCCACAG GGTCTCCCTA CCAGTTCCAG GTCCTGGAA GTGGGGGACTC ACACAGGT TCACACAGGT TCTTAGTCC TTCTTAGTCC
155 LysCysArg ThrGlyCysP roArgGlyMe tValLysVal GlyAspCysT hrProTrpSe rAspIleGlu CysValHisL ysGluSerGl yIleIleIle

701 GGAGTCACAG TTGCAGCCGT AGTCTTGATT GTGGCTGTGT TTGTTTGCAA GTCTTACTG TGGAAGAAAG TCCTTCCTTA CCTGAAAGGC ATCTGCTCAG
    CCTCAGTGTC AACGTCGGCA TCAGAACTAA CACCGACACA AACAAACGTT CAGAAATGAC ACCTTCTTTC AGGAAGGAAT GGACTTTCCG TAGACGAGTC
188 GlyValThrV alAlaAlaVa lValLeuIle ValAlaValP heValCysLy sSerLeuLeu TrpLysLysV alLeuProTy rLeuLysGly IleCysSerGly

801 GTGGTGGTGG GGACCCTGAG CGTGTGGACA GAAGCTCACA ACGACCTGGG GCTGAGGACA ATGTCCTCAA TGAGATCGTG AGTATCTTGC AGCCCACCA
    CACCACCACC CCTGGGACTC GCACACCTGT CTTCGAGTGT TGCTGGACCC CGACTCCTGT TACAGGAGTT ACTCTAGCAC TCATAGAACG TCGGGTGGGT
222 GlyGlyGl yAspProGl nArgSerGl rgSerSerGl nArgValAspA rgArgProGly AlaGluAspA snValLeuAs nGluIleVal SerIleLeuG lnProThrGln
```

FIG._5A

```
 901 GGTCCCTGAG CAGGAAATGG AAGTCCAAGGA GCCAGCAGAG CCAACAGGTG TCAACATGTT GTCCCCCGGG GAGTCAGAGC ATCTGCTGGA ACCGGCAGAA
     CCAGGGACTC GTCCTTACC  TTCAGGTCCT CGGTCGTCTC GGTTGTCCAC AGTTGTACAA CAGGGGGCCC CTCAGTCTCG TAGACGACCT TGGCCGTCTT
 255 ValProGlu GlnGluMetG luValGlnGl uProAlaGlu ProThrGlyV alAsnMetLe uSerProGly GluSerGluH isLeuLeuGl uProAlaGlu

1001 GCTGAAAGGT CTCAGAGGAG GAGGCTGCTG GTTCCAGCAA ATGAAGGTGA TCCCACTGAG ACTCTGAGAC AGTGCTTCGA TGACTTGCA  GACTTGGTGC
     CGACTTTCCA GAGTCTCCTC CTCCGACGAC CAAGGTCGTT TACTTCCACT AGGGTGACTC TGAGACTCTG TCACGAAGCT ACTGAAACGT CTGAACCACG
 288 AlaGluArgS erGlnArgAr gArgLeuLeu ValProAlaA snGluGlyAs pProThrGlu ThrLeuArgG lnCysPheAs pAspPheAla AspLeuValPro

1101 CCTTTGACTC CTGGGAGCCG CTCATGAGGA AGTTGGGCT  CATGGACAAT GAGATAAAGC TGGCTAAAGC TGAGCCAGCG GGCCACAGGG ACACCTTGTA
     GGAAACTGAG GACCCTCGGC GAGTACTCCT TCAACCCGGA GTACCTGTTA CTCTATTTCC ACCGATTTCG ACTCCGTCCC CCGGTGTCCC TGTGGAACAT
 322 PheAspSe   rTrpGluPro LeuMetArgL ysLeuGlyLe uMetAspAsn GluIleLysV alAlaLysAl aGluAlaAla GlyHisArgA spThrLeuTyr

1201 CACGATGCTG ATAAAGTGGG TCAACAAAAC CGGGCGAGAT GCCTCTGTCC ACACCCTGCT GGATGCCTTG GAGACGCTGG TGCCAAGCAG
     GTGCTACGAC TATTTCACCC AGTTGTTTTG GCCCGCTCTA CGGAGACAGG TGTGGGACGA CCTACGGAAC CTCTGCGACC ACGGTTCGTC
 355 ThrMetLeu  IleLysTrpV alAsnLysTh rGlyArgAsp AlaSerValH isThrLeuLe uAspAlaLeu GluThrLeuG luProSerGln

1301 AAGATTGAGG ACCACTTGTT GAGCTCTGGA AAGTTCATGT TAATGCAGAC TCTGCCWTGT CCTAAGTGTG ATTCTCTTCA GGAAGTGAGA
     TTCTAACTCC TGGTGAACAA CTCGAGACCT TTCAAGTACA ATTACGTCTG AGACGGAACA GGATTCACAC TAAGAGAAGT CCTTCACTCT
 388 LysIleGluA spHisLeuLe uSerSerGly LysPheMetT yrLeuGluGl yAsnAlaAsp SerAlaXaaS erOC*

1401 CCTTCCCTGG TTTACTTTT  TTCTGAAAAA AGCCCAACTG GACTCCAGTC AGTAGGAAAG TGCCACAATT GTCACATGAC CGGTACTGAC AGAAACTCTC
     GGAAGGGACC AAATGAAAA  AAGACTTTTT TCGGGTTGAC CTGAGGTCAG TCATCCTTTC ACGGTGTTAA CAGTGTACTG GCCATGACCT TCTTTGAGAG

1501 CCATCCAACA TCACCCAGTG GATGGAACAT CCTGTAACTT TTCACTGCAC TTGGCATTAT TTTATATAAGC TGAATGTGAT AATAAGGACA CTATGGAAAT
     GGTAGGTTGT AGTGGGTCAC CTACCTTGTA GGACATTGAA AAGTGACGTG AACCGTAATA AAAATATTCG ACTTACACTA TTATTCCTGT GATACCTTTA

1601 GTCTGGATCA TTCCGTTTGT AGATTTGGTT TGGGATGTCA TTGTTTTCAC AGCACTTTTT TATCCTAATG TAAATGCTTT ATTTATTAT
     CAGACCTAGT AAGGCAAACA TCTAAACAAC ACCCTACAGT AACAAAAGTG TCGTGAAAAA ATAGGATTAC ATTTACGAAA TAAATAAATA

1701 TTGGGCTACA TTGTAAGATC CATCTACACA AAAAAAAAAAG GGCGGCCGCG ACTCTAGAGT CGACCTGCAG AAGCTTGGCC GCCATGGCC
     AACCCGATGT AACATTCTAG GTAGATGTTT TTTTTTTTTTC CCGCCGGCGC TGAGATCTCA GCTGGACGTC TTCGAACCGG CGGTACCGG
```

FIG._5B

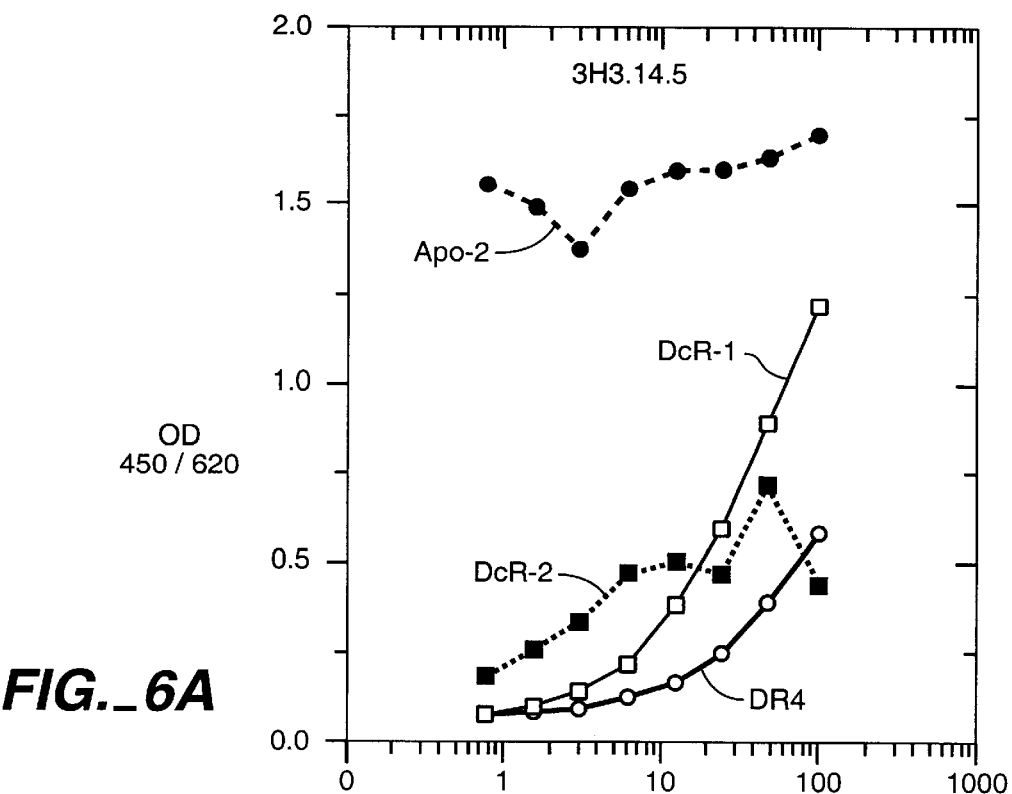
FIG._6A
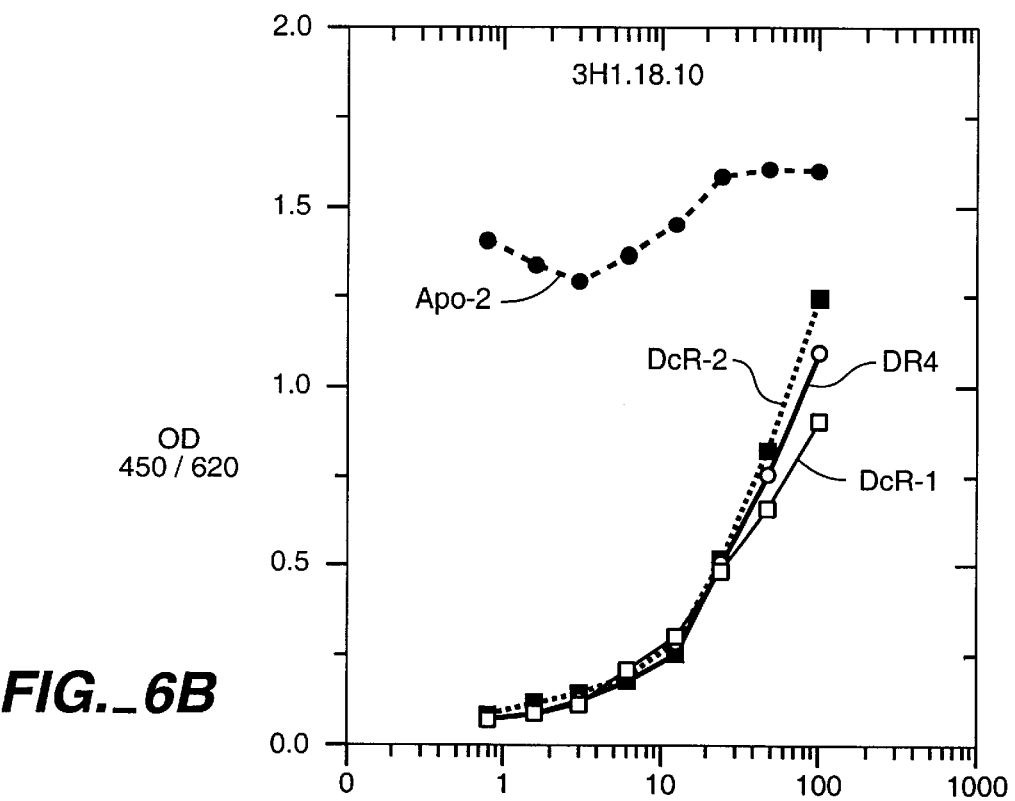
FIG._6B

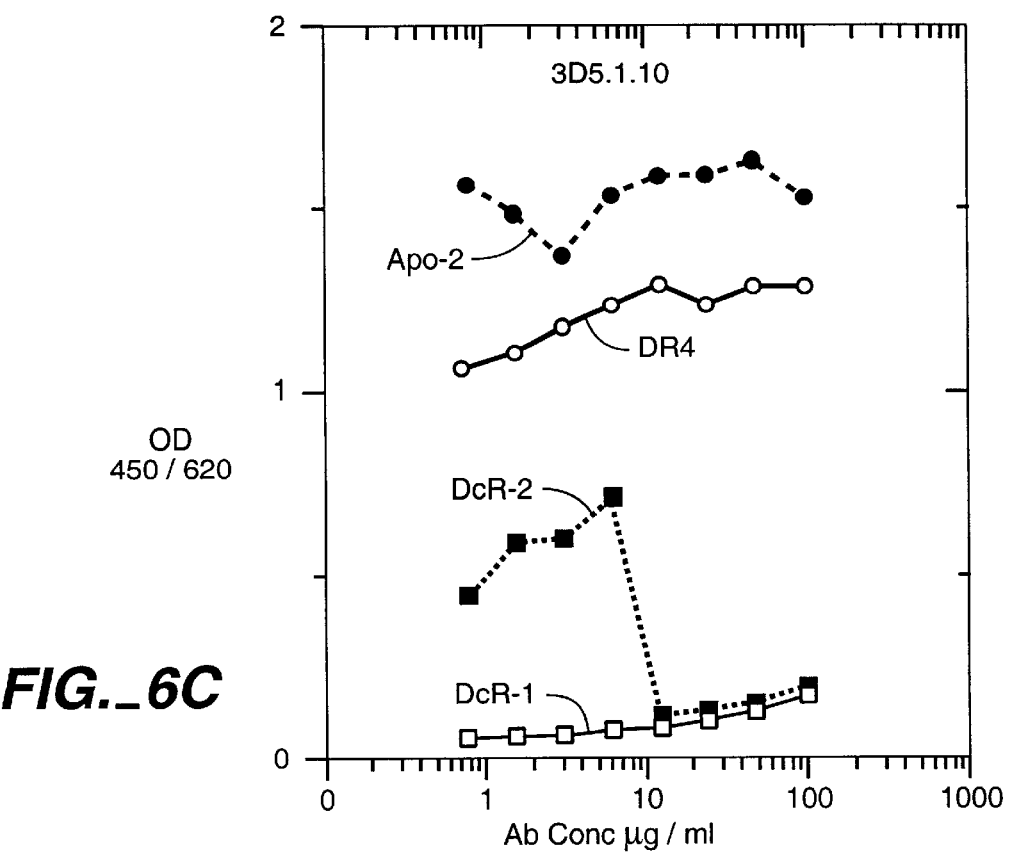
FIG._6C
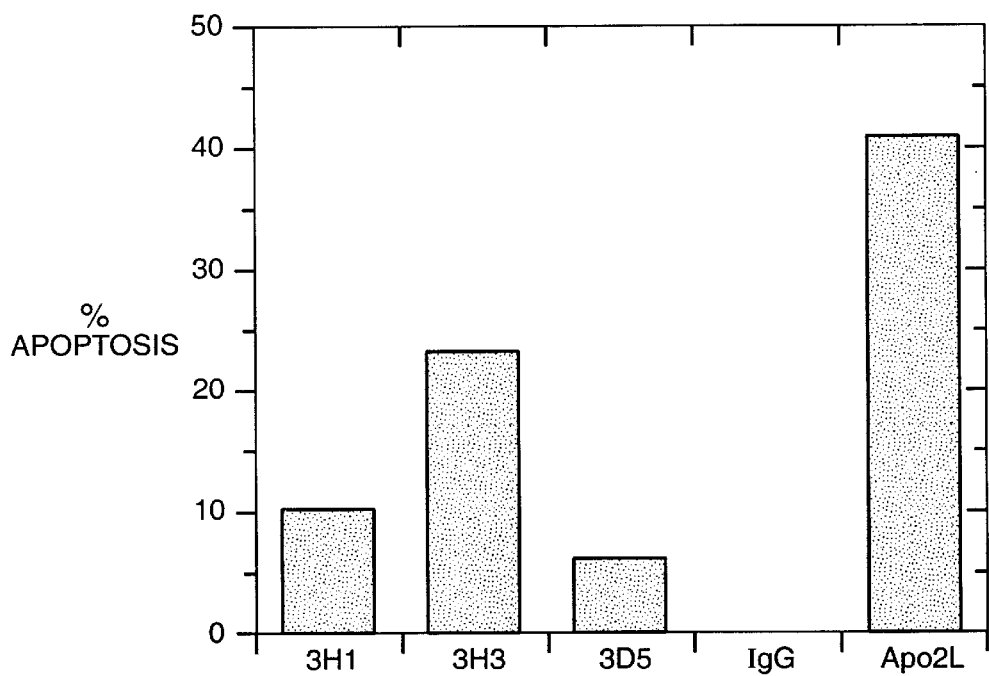
FIG._8

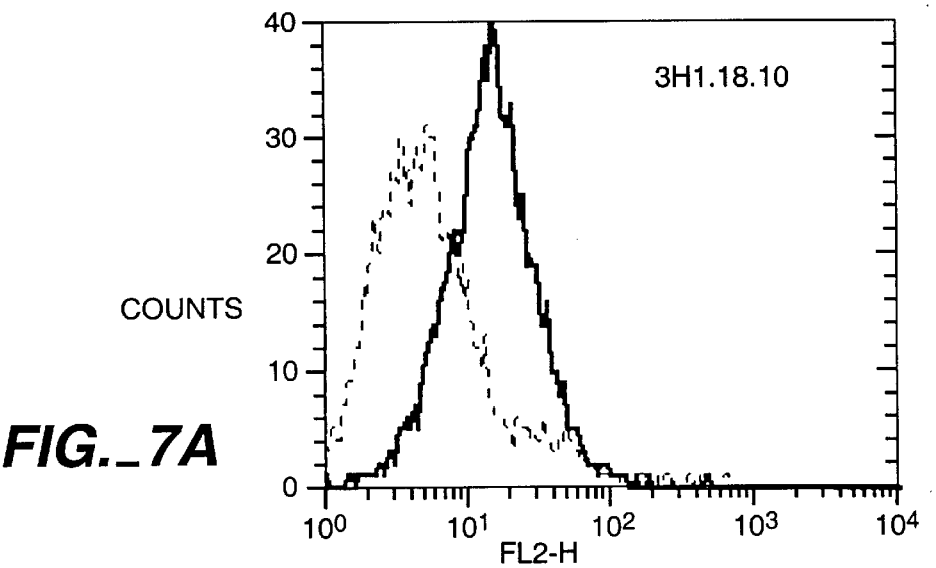
FIG._7A
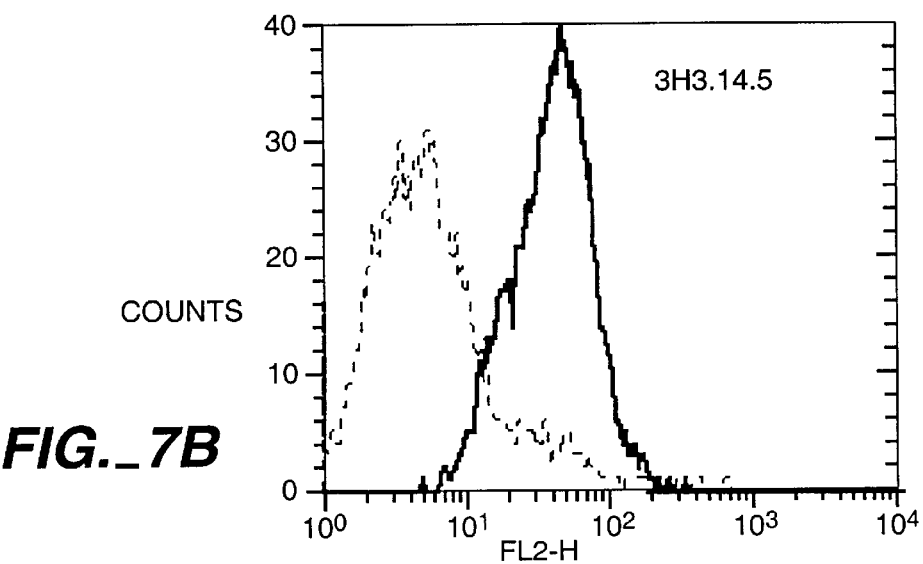
FIG._7B
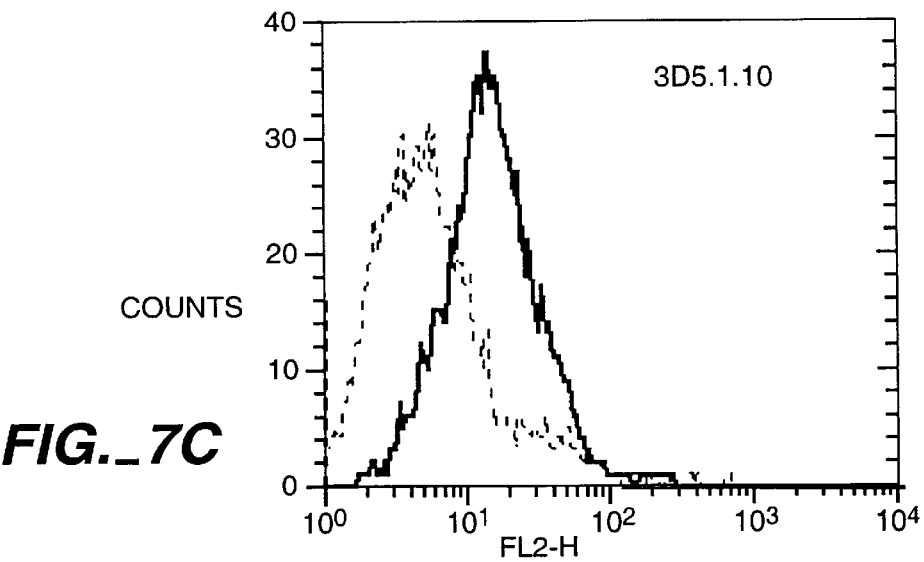
FIG._7C

METHOD FOR MAKING MONOCLONAL ANTIBODIES AND CROSS-REACTIVE ANTIBODIES OBTAINABLE BY THE METHOD

RELATED APPLICATION

This application is a non-provisional application filed under 37 CFR 1.53(b)(1), claiming priority under 35 USC 119(e) to provisional application number 60/089,253 filed Jun. 12, 1998, the contents of which are incorporated herein by reference.

BACKGROUND OF THE INVENTION

1. Field of the Invention

This invention relates generally to a method for making monoclonal antibodies. The invention further pertains to antibodies obtainable by the method which specifically cross-react with two or more different receptors to which Apo-2 ligand (Apo-2L) can bind.

2. Description of Related Art

Native antibodies are synthesized primarily by specialized lymphocytes called "plasma cells". Production of a strong antibody response in a host animal is controlled by inducing and regulating the differentiation of B cells into these plasma cells. This differentiation involves virgin B cells (which have a modified antibody as a cell-surface antigen receptor and do not secrete antibodies) becoming activated B cells (which both secrete antibodies and have cell-surface antibodies), then plasma cells (which are highly specialized antibody factories with no surface antigen receptors). This differentiation process is influenced by the presence of antigen and by cellular communication between B cells and helper T cells.

Because of their ability to bind selectively to an antigen of interest, antibodies have been used widely for research, diagnostic and therapeutic applications. The potential uses for antibodies were expanded with the development of monoclonal antibodies. In contrast to polyclonal antiserum, which includes a mixture of antibodies directed against different epitopes, monoclonal antibodies are directed against a single determinant or epitope on the antigen and are homogeneous. Moreover, monoclonal antibodies can be produced in unlimited quantities.

The seminal work by Kohler and Milstein described the first method for obtaining hybridomas that can produce monoclonal antibodies [Kohler and Milstein *Nature* 256:495 (1975)]. In this method, an antibody-secreting immune cell, isolated from an immunized mouse, is fused with a myeloma cell, a type of B cell tumor. The resultant hybrid cells (i.e. hybridomas) can be maintained in vitro and continue to secrete antibodies with a defined specificity.

Since murine monoclonal antibodies are derived from mice, their use as therapeutic agents in humans is limited because of the human anti-mouse response that occurs upon administration of the murine antibody to a patient. Accordingly, researchers have engineered non-human antibodies to make them appear more human. Such engineered antibodies are called "chimeric" antibodies; in which a non-human antigen-binding domain is coupled to a human constant domain (Cabilly et al., U.S. Pat. No. 4,816,567). The isotype of the human constant domain may be selected to tailor the chimeric antibody for participation in antibody-dependent cellular cytotoxicity (ADCC) and complement-dependent cytotoxicity. In a further effort to resolve the antigen binding functions of antibodies and to minimize the use of heterologous sequences in human antibodies, Winter and colleagues [(Jones et al., *Nature* 321:522–525 (1986); Riechmann et al., *Nature* 332:323–327 (1988); Verhoeyen et al., *Science* 239:1534–1536 (1988)] have substituted rodent complementarity determining region (CDR) residues for the corresponding segments of a human antibody to generate humanized antibodies. As used herein, the term "humanized" antibody is an embodiment of chimeric antibodies wherein substantially less than an intact human variable domain has been substituted by the corresponding sequence from a non-human species. In practice, humanized antibodies are typically human antibodies in which CDR residues and possibly some framework region (FR) residues are substituted by residues from analogous sites in rodent antibodies.

Other groups have developed methods for making fully "human" monoclonal antibodies. Such antibodies may be generated by immortalizing a human cell secreting a specific antibody using an Epstein-Barr virus (EBV) [Steinitz et al. *Nature* 269:420–422 (1977)]; or by preparing a human—human hybridoma secreting the monoclonal antibody [Olsson et al. *PNAS (USA)* 77:5429–5431 (1980)]. Human antibodies can also be derived from phage-display libraries [Hoogenboom et al., *J. Mol. Biol.*, 227:381 (1991); Marks et al., *J. Mol. Biol.*, 222:581–597 (1992); Vaughan et al. *Nature Biotech* 14:309 (1996)].

Alternatively, human antibodies have been made in transgenic laboratory animals, in which human immunoglobulin loci have been introduced into the animal and the endogenous immunoglobulin genes are partially or completely inactivated [Fishwild et al. *Nature Biotech*. 14:845–851 (1996); and Mendez et al. *Nature Genetics* 15:146–156 (1997)].

SUMMARY OF THE INVENTION

The present invention, in one aspect, provides a method for making monoclonal antibodies wherein an animal is immunized with two or more different antigens and monoclonal antibodies are made and identified which bind to each antigen. Surprisingly, it was discovered herein that sera titers from animals immunized with a mixture of different antigens were similar to those achieved in animals immunized with a single antigen.

This method is thought to be useful for reducing the number of animals that need to be immunized and sacrificed in order to make two or more monoclonal antibodies with differing antigen-binding specificities.

Moreover, it was discovered that the method was useful for making antibodies that cross-reacted with two or more different antigens. For example, antibodies were made which specifically cross-reacted with two or more different Apo-2L receptors.

Accordingly, the invention provides a method for making antibodies comprising the following steps:

(a) immunizing an animal with two or more different antigens so as to generate polyclonal antibodies against each antigen in the animal;

(b) preparing monoclonal antibodies using immune cells of the immunized animal which produce said polyclonal antibodies; and (c) screening said monoclonal antibodies to identify one or more monoclonal antibodies that bind to each antigen. In the screening step, one finds at least one monoclonal antibody against at least two different antigens. Preferably, at least one monoclonal antibody is found for each antigen with which the animal was immunized.

Preferably, the animal is immunized with a composition comprising a mixture of the two or more different antigens; and step (b) comprises fusing immune cells from the immunized animal with myeloma cells in order to generate hybridoma cell lines producing the monoclonal antibodies.

In one embodiment, the method further comprises identifying one or more monoclonal antibodies that cross-react with two or more of the different antigens.

The invention further provides a monoclonal antibody that has been made according to the above method (e.g. one that cross-reacts with two or more structurally or functionally related antigens).

The invention also relates to an antibody that specifically cross-reacts with two or more different Apo-2L receptors; e.g. which specifically binds to Apo-2 polypeptide and further specifically cross-reacts with another Apo-2L receptor.

The present application further supplies a monoclonal antibody which has the biological characteristics of a monoclonal antibody selected from the group consisting of 3H1.18.10, 3H3.14.5 and 3D5.1.10.

Moreover, the invention provides hybridoma cell lines that produce any of the monoclonal antibodies disclosed herein.

The invention also relates to isolated nucleic acid comprising DNA encoding an antibody as herein disclosed; a vector comprising the nucleic acid; a host cell comprising the vector; a method of producing an antibody comprising culturing the host cell under conditions wherein the DNA is expressed and, optionally, further comprising recovering the antibody from the host cell culture.

The invention further provides a composition comprising an antibody as described herein and a carrier.

In addition, a method of inducing apoptosis in mammalian cancer cells is provided which comprises exposing mammalian cancer cells to an effective amount of a cross-reactive, agonistic anti-Apo-2L receptor antibody as disclosed herein.

The invention further pertains to an article of manufacture comprising a container and a composition contained within said container, wherein the composition includes an antibody as described herein.

BRIEF DESCRIPTION OF THE DRAWINGS

FIG. 1 depicts an exemplary mixed antigen immunization scheme for the immunogens: Apo-2-IgG, DR4-IgG, DcR1-IgG and DcR2-IgG.

FIG. 2 illustrates single antigen immunization schemes for the antigens: Apo-2-IgG, DR4-IgG and DcR2-IgG.

FIG. 3 shows antigen specific sera titers of mice immunized with DR4-IgG, Apo-2-IgG or DcR2-IgG individually. Sera were collected from Balb/c mice (5 mice/group) which were immunized 10 times into Foot Pad (F.P.) with 1 $\mu$g of each immunoadhesin molecule in MPL-TDM. The activity toward human IgG Fc portion was preadsorbed by incubating 100 ml of sera (1:500 dilution in PBS) with 3 mg per 50 ml of CD4-IgG for 1 hr at room temperature (RT). Serial dilutions of this preadsorbed sera were than prepared in PBS. The antigen specific activities of this preadsorbed-sera were determined in a capture ELISA using the specific antigen coated microtiter wells.

FIG. 4 shows antigen specific sera titers of mice immunized with DR4-IgG, Apo-2-IgG, DcR1-IgG and DcR2-IgG together. Mice were immunized into F.P. with a mixture of DR4-IgG, Apo-2-IgG, DcR1-IgG and DcR2-IgG (mice were immunized 14 times; DcR2-IgG was only included in the mixture for the final 6 immunizations). 1 $\mu$g per injection of each immunogen was used. The activity to human IgG Fc in the sera was adsorbed by incubating with CD4-IgG as described above. The activity of this preadsorbed sera specific for each antigen was determined in a capture ELISA using the microtiter wells coated with the specific antigen.

FIGS. 5A and 5B show the nucleotide sequence of a native sequence human Apo-2 cDNA (SEQ ID NO:1) and its derived amino acid sequence (SEQ ID NO:2).

FIGS. 6A, 6B and 6C depict antibody binding to Apo2-L receptors: DR4, Apo-2, DcR1 and DcR2 as determined by ELISA. The antibodies are: 3H3.14.5 (FIG. 6A), 3H1.18.10 (FIG. 6B), and 3D5.1.10 (FIG. 6C).

FIGS. 7A, 7B and 7C show FACS analysis for antibodies 3H1.18.10 (FIG. 7A), 3H3.14.5 (FIG. 7B), and 3D5.1.10 (FIG. 7C) [illustrated by bold lines] as compared to IgG controls [dotted lines]. The antibodies all recognized Apo-2 expressed in human 9D cells.

FIG. 8 depicts apoptosis induced by antibodies 3H1.18.10 (3H1), 3H3.14.5 (3H3) and 3D5.1.10 (3D5), an isotype-matched control (IgG), and Apo-2L.

DETAILED DESCRIPTION OF THE PREFERRED EMBODIMENTS

I. Definitions

The term "antibody" is used in the broadest sense and specifically covers monoclonal antibodies (including agonist, antagonist, and blocking or neutralizing antibodies) and antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an antibody with a constant domain, or a light chain with a heavy chain, or a chain from one species with a chain from another species, or fusions with heterologous proteins, regardless of species of origin or immunoglobulin class or subclass designation, as well as antibody fragments (e.g., Fab, Fab', F(ab')$_2$, and Fv), so long as they exhibit the desired biological activity. See, e.g. U.S. Pat. No. 4,816,567 and Mage et al., in *Monoclonal Antibody Production Techniques and Applications*, pp.79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies of the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552–554 (1990), for example.

"Single-chain Fv" or "scFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see, e.g., Pluckthun, *The Pharmacology of Monoclonal Antibodies*, vol. 113, Rosenburg and Moore eds. Springer-Verlag, New York, pp. 269–315 (1994).

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody or the donor antibody. These modifications are made to further refine and optimize antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

The term "hypervariable region" when used herein refers to the amino acid residues of an antibody which are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. residues 26–32 (L1), 50–52 (L2) and 91–96 (L3) in the light chain variable domain and 26–32 (H1), 53–55 (H2) and 96–101 (H3) in the heavy chain variable domain; Chothia and Lesk *J. Mol. Biol.* 196:901–917 (1987)). "Framework" or "FR" residues are those variable domain residues other than the hypervariable region residues as herein defined.

The terms "Apo-2 ligand" or "Apo-2L" refer to the Apo-2L polypeptides disclosed in WO97/25428, published Jul. 17, 1997 and expressly incorporated herein by reference. For purposes of the present application, these terms also refer to the polypeptides disclosed in WO97/01633, published Jan. 16, 1997 and expressly incorporated herein by reference.

An "Apo-2L receptor" is a polypeptide to which Apo-2L (as herein defined) can specifically bind. The term "Apo-2L receptor" when used herein encompasses native sequence Apo-2L receptors and variants thereof (which are further defined herein). These terms encompass Apo-2L receptor from a variety of mammals, including humans. The Apo-2L receptor may be isolated from a variety of sources, such as from human tissue types or from another source, or prepared by recombinant or synthetic methods. Examples of "native sequence" Apo-2L receptors include Apo-2 polypeptide (as described herein below), native sequence "DR4" as described in Pan et al. *Science* 276:111–113 (1997); native sequence "decoy receptor 1" or "DcR1" as in Sheridan et al., *Science* 277:818–821 (1997); and native sequence "decoy receptor 2" or "DcR2" as in Marsters et al. *Curr. Biol.* 7:1003–1006 (1997) and native sequence osteoprotegerin [see Simonet et al. *Cell* 89:309–319 (1997) and Emery et al. *J. Interferon and Cytokine Research* 18(5): A47 Abstract 2.17 (1998)].

The terms "Apo-2 polypeptide" and "Apo-2" when used herein encompass native sequence Apo-2 and Apo-2 variants (which are further defined herein). These terms encompass Apo-2 from a variety of mammals, including humans. The Apo-2 may be isolated from a variety of sources, such as from human tissue types or from another source, or prepared by recombinant or synthetic methods.

A "native sequence" polypeptide (e.g. "native sequence Apo-2") comprises a polypeptide having the same amino acid sequence as a polypeptide derived from nature. Thus, a native sequence polypeptide can have the amino acid sequence of naturally-occurring polypeptide from any mammal. Such native sequence polypeptide can be isolated from nature or can be produced by recombinant or synthetic means. The term "native sequence" polypeptide specifically encompasses naturally-occurring truncated or secreted forms of the polypeptide (e.g., an extracellular domain sequence), naturally-occurring variant forms (e.g., alternatively spliced forms) and naturally-occurring allelic variants of the polypeptide.

A naturally-occurring variant form of Apo-2 includes an Apo-2 having an amino acid substitution at residue 410 in the amino acid sequence shown in FIG. 5 (SEQ ID NO:2). In one embodiment of such naturally-occurring variant form, the leucine residue at position 410 is substituted by a methionine residue. In FIG. 5 (SEQ ID NO:2), the amino acid residue at position 410 is identified as "Xaa" to indicate that the amino acid may, optionally, be either leucine or methionine. In FIG. 10 (SEQ ID NO:2), the nucleotide at position 1367 is identified as "W" to indicate that the nucleotide may be either adenine (A) or thymine (T) or uracil (U). In one embodiment of the invention, the native sequence Apo-2 is a mature or full-length native sequence Apo-2 comprising amino acids 1 to 411 of FIG. 5 (SEQ ID NO:2). Optionally, the Apo-2 is obtained or obtainable by expressing the polypeptide encoded by the cDNA insert of the vector deposited as ATCC 209021.

An "extracellular domain" or "ECD" (e.g. "Apo-2 extracellular domain" or "Apo-2. ECD") refers to a form of a receptor polypeptide which is essentially free of the transmembrane and cytoplasmic domains of the receptor. Ordinarily, the ECD will have less than 1% of such transmembrane and/or cytoplasmic domains and preferably, will have less than 0.5% of such domains. Optionally, Apo-2 ECD will comprise amino acid residues 54 to 182 of FIG. 5 (SEQ ID NO:2) or amino acid residues 1 to 182 of FIG. 5 (SEQ ID NO:2). Optionally, Apo-2 ECD will comprise one or more cysteine-rich domains, and preferably, one or both of the cysteine-rich domains identified for the sequence shown in Sheridan et al., *Science* 277:818–821 (1997). It will be understood by the skilled artisan that the transmembrane domain identified for the Apo-2 polypeptide herein is identified pursuant to criteria routinely employed in the art for identifying that type of hydrophobic domain. The exact boundaries of a transmembrane domain may vary but most likely by no more than about 5 amino acids at either end of the domain specifically mentioned herein.

A polypeptide "variant" (e.g. "Apo-2 variant") means a biologically active polypeptide having at least about 80% amino acid sequence identity with the native sequence polypeptide, e.g. with Apo-2 having the deduced amino acid sequence shown in FIG. 5 (SEQ ID NO:2) for a full-length native sequence human Apo-2 or the sequences identified herein for Apo-2 ECD or death domain. Such variants include, for instance, polypeptides wherein one or more amino acid residues are added, or deleted, at the N- or C-terminus of the polypeptide [e.g. in the case of Apo-2 in the sequence of FIG. 5 (SEQ ID NO:2) or the sequences identified herein for Apo-2 ECD or death domain].

Examples of "antibody variants" include humanized variants of non-human antibodies, "affinity matured" antibodies (see, e.g. Hawkins et al. *J. Mol. Biol.* 254: 889–896 [1992] and Lowman et al. *Biochemistry* 30(45): 10832–10837 [1991]) and antibody mutants with altered effector function (s) (see, e.g., U.S. Pat. No. 5,648,260 issued on Jul. 15, 1997, expressly incorporated herein by reference).

Ordinarily, a variant will have at least about 80% amino acid sequence identity, more preferably at least about 90% amino acid sequence identity, and even more preferably at least about 95% amino acid sequence identity with native sequence [e.g. for Apo-2, with the amino acid sequence of FIG. 5 (SEQ ID NO:2) or the sequences identified herein for Apo-2 ECD or death domain].

"Percent (%) amino acid sequence identity" is defined as the percentage of amino acid residues in a candidate sequence that are identical with the amino acid residues in the native sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGNT or Megalign (DNASTAR) software. Those skilled in the art can determine appropriate parameters for measuring alignment, including any algorithms needed to achieve maximal alignment over the full length of the sequences being compared.

The term "epitope tagged" when used herein refers to a plypeptide, or a domain sequence thereof, fused to a "tag polypeptide". The tag polypeptide has enough residues to provide an epitope against which an antibody can be made, yet is short enough such that it does not interfere with activity of the polypeptide. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

"Biologically active" and "desired biological activity" with respect to an Apo-2L receptor for the purposes herein means (1) having the ability to modulate apoptosis (either in an agonistic or stimulating manner or in an antagonistic or blocking manner) in at least one type of mammalian cell in vivo or ex vivo; (2) having the ability to bind Apo-2 ligand; or (3) having the ability to modulate Apo-2 ligand signaling and Apo-2 ligand activity.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis, all of which are known in the art.

The terms "treating," "treatment," and "therapy" as used herein refer to curative therapy, prophylactic therapy, and preventative therapy.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, blastoma, gastrointestinal cancer, renal cancer, pancreatic cancer, glioblastoma, neuroblastoma, cervical cancer, ovarian cancer, liver cancer, stomach cancer, bladder cancer, hepatoma, breast cancer, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer.

The term "mammal" as used herein refers to any mammal classified as a mammal, including humans, cows, horses, dogs and cats.

The terms "antigen" and "immunogen" are used interchangeably herein to refer to a molecule or substance which induces an immune response (preferably an antibody response) in an animal immunized therewith (i.e. the antigen is "immunogenic" in the animal). The antigen may be a protein, peptide, carbohydrate, nucleic acid, lipid, hapten or other naturally occurring or synthetic compound. Preferably the antigen is a "protein" having a molecular weight of greater than about 4 kD. The protein may, for example, be a cellular, bacterial or viral protein.

By "different antigens" is meant antigens that are structurally distinct; e.g., in the case of peptides or proteins, having different amino acid sequences.

The expression "structurally or functionally related antigens" refers to antigens with similar structures and/or similar functions. For example, the antigens may comprise receptors (or fragments thereof), optionally fused to heterologous amino acid sequences, which are bound by and/or activated by the same ligand, e.g., Apo-2L receptors as described herein. Other examples of structurally and functionally related receptors include members of the ErbB2 receptor family, such as the EGF receptor, HER2, HER3 and HER4 receptor; and members of the Rse, Axl and Mer receptor family. Examples of structurally or functionally related ligands include the neuregulins, insulin-like growth factors (IGFs), etc.

The protein antigen of interest may be a "receptor" [i.e. a protein molecule which exists in nature on a cell surface or within the cytoplasm of a cell and which is capable of binding to one or more ligand(s)]. Another exemplary antigen is a protein "ligand" [i.e. a molecule capable of binding to and, optionally, activating one or more receptor(s); e.g. a growth factor]. The antigen herein may, for example, comprise a fragment of a receptor or ligand, optionally fused to one or more heterologous amino acid sequences (e.g. the antigen may be an immunoadhesin).

As used herein, the term "immunoadhesin" designates antibody-like molecules which combine the "binding domain" of a heterologous "adhesin" protein (e.g. a receptor, ligand or enzyme) with an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. See, e.g., U.S. Pat. No. 5,565,335 and U.S. Pat. No. 5,116,964, expressly incorporated herein by reference.

The term "ligand binding domain" as used herein refers to any native cell-surface receptor or any region or derivative thereof retaining at least a qualitative ligand binding ability of a corresponding native receptor. In a specific embodiment, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selecting.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule that combines at least one binding domain of an antibody (as herein defined) with at least one immunoadhesin (as defined in this application). Exemplary antibody-immunoadhesin chimeras are the bispecific CD4-IgG chimeras described in Berg et al., *PNAS (USA)* 88:4723–4727 (1991) and Chamow et al., *J. Immunol.* 153:4268 (1994).

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

A "purified" antigen is one which has been subjected to one or more purification procedures. The purified antigen may be "homogeneous", which is used herein to refer to a composition comprising, at least about 70% to about 100% by weight of the antigen of interest, based on total weight of the composition, preferably at least about 80% to about 100% by weight of the antigen of interest.

The term "immunizing" refers to the step or steps of administering one or more antigens to an animal so that antibodies can be raised in the animal. Generally, immunizing comprises injecting the antigen or antigens into the animal. Immunization may involve one or more administrations of the antigen or antigens.

The "animal" to be immunized herein is preferably a rodent. Other animals which can be immunized herein include non-human primates such as Old World monkey (e.g. baboon or macaque, including Rhesus monkey and cynomolgus monkey; see U.S. Pat. No. 5,658,570); birds (e.g. chickens); rabbits; goats; sheep; cows; horses; pigs; donkeys; dogs etc.

A "rodent" is an animal belonging to the rodentia order of placental mammals. Exemplary rodents include mice, rats, guinea pigs, squirrels, hamsters, ferrets etc, with mice being the preferred rodent for immunizing according to the method herein.

"Polyclonal antibodies" or "polyclonal antisera" refer to immune serum containing a mixture of antibodies specific for one (monovalent or specific antisera) or more (polyvalent antisera) antigens which may be prepared from the blood of animals immunized with the antigen or antigens.

The term "immune cells" refers to cells which are capable of producing antibodies. The immune cells of particular interest herein are lymphoid cells derived, e.g. from spleen, peripheral blood lymphoctes (PBLs), lymph node, inguinal node, Peyers patch, tonsil, bone marrow, cord blood, pleural effusions and tumor-infiltrating lymphocytes (TIL).

By "solid phase" is meant a nonaqueous matrix to which a molecule of interest can specifically or nonspecifically adhere (e.g., an assay plate).

An "adjuvant" is a nonspecific stimulant of the immune response. The adjuvant may be in the form of a composition comprising either or both of the following components: (a) a substance designed to form a deposit protecting the antigen(s) from rapid catabolism (e.g. mineral oil, alum, aluminium hydroxide, liposome or surfactant [e.g. pluronic polyol]) and (b) a substance that nonspecifically stimulates the immune response of the immunized host animal (e.g. by increasing lymphokine levels therein). Exemplary molecules for increasing lymphokine levels include lipopolysaccaride (LPS) or a Lipid A portion thereof; Bordetalla pertussis; pertussis toxin; *Mycobacterium tuberculosis*; and muramyl dipeptide (MDP). Examples of adjuvants include Freund's adjuvant (optionally comprising killed *M. tuberculosis*; complete Freund's adjuvant); aluminium hydroxide adjuvant; and monophosphoryl Lipid A-synthetic trehalose dicorynomylcolate (MPL-TDM).

By "screening" is meant subjecting one or more monoclonal antibodies (e.g., purified antibody and/or hybridoma culture supernatant comprising the antibody) to one or more assays which determine qualitatively and/or quantitatively the ability of an antibody to bind to an antigen of interest.

By "immuno-assay" is meant an assay that determines binding of an antibody to an antigen, wherein either the antibody or antigen, or both, are optionally adsorbed on a solid phase (i.e., an "immunoadsorbent" assay) at some stage of the assay. Exemplary such assays include ELISAs, radioimmunoassays (RIAs), and FACS assays.

An antibody which "cross-reacts" with two or more different antigens is capable of binding to each of the different antigens, e.g. as determined by ELISA or FACS as in the examples below.

An antibody which "'specifically cross-reacts" with two or more different antigens is one which binds to a first antigen and further binds to a second different antigen, wherein the binding ability (e.g. OD 450/620; FIGS. 6A–C) of the antibody for the second antigen at an antibody concentration of about 10 μg/mL is from about 50% to about 100% (preferably from about 75% to about 100%) of the binding ability of the first antigen as determined in a capture ELISA as in the examples below. For example, the antibody may bind specifically to Apo-2 (the "first antigen") and specifically cross-react with another Apo-2L receptor such as DR4 (the "second antigen"), wherein the extent of binding of about 10 μg/mL of the antibody to DR4 is about 50% to about 100% of the binding ability of the antibody for Apo-2 in the capture ELISA herein.

The word "label" when used herein refers to a detectable compound or composition which can be conjugated directly or indirectly to a molecule of interest and may itself be detectable (e.g., radioisotope labels or fluorescent labels) or, in the case of an enzymatic label, may catalyze chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or variants and/or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (TAXOL™, Bristol-Myers Squibb Oncology, Princeton, N.J.), and doxetaxel (Taxotere, Rhône-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

The term "prodrug'" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375–382, 615th Meeting Belfast (1986) and Stella et al., "Prodrugs: A Chemical Approach to Targeted Drug Delivery," *Directed Drug Delivery*, Borchardt et al., (ed.), pp. 247–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, -lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

Modes for Carrying Out the Invention

A. Mixed Antigen Immunization Protocol

In one aspect, the invention provides a method for making monoclonal antibodies wherein an animal is immunized with two or more different antigens so as to generate polyclonal antibodies, and preferably monoclonal antibodies, against the two or more antigens with which the animal was immunized. This method will be described in more detail in the following sections.

(i) Antigen selection and preparation

The method herein involves preparation of antibodies directed against one or more different antigens. Preferably, at least one of the antigens is (and preferably all of the antigens are) is a biologically important molecule and administration of an antibody thereagainst to a mammal suffering from a disease or disorder can result in a therapeutic benefit in that mammal. In the preferred embodiment of the invention, the antigen is a protein. However, other nonpolypeptide antigens (e.g. tumor associated glycolipids; see U.S. Pat. No. 5,091,178) may be used.

Exemplary protein antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and variants and/or fragments of any of the above-listed polypeptides.

Preferred molecular targets for antibodies encompassed by the present invention include CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150.95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C; an Apo-2L receptor such as Apo-2, DR4, DcR1 and DcR2; and variants and/or fragments of the above-identified molecules etc.

Each antigen to be used in the method is preferably purified to form an essentially homogeneous preparation of the antigen using purification techniques available in the art. Examples of purification procedures which can be used include fractionation on a hydrophobic interaction chromatography (e.g. on phenyl sepharose), ethanol precipitation, isoelectric focusing, Reverse Phase HPLC, chromatography on silica, chromatography on HEPARIN SEPHAROSE™, anion exchange chromatography, cation exchange chromatography, chromatofocusing, SDS-PAGE, ammonium sulfate precipitation, hydroxylapatite chromatography, gel electrophoresis, dialysis, affinity chromatography (e.g. using protein A, protein G, an antibody, a specific substrate, ligand or antigen as the capture reagent) or combinations of two or more of these methods.

In the case of a protein antigen, an immunoadhesin may be prepared by fusing the protein (or a fragment thereof) to an immunoglobulin Fc region and purifying the resultant immunoadhesin by Protein A or Protein G chromatography.

Soluble antigens or fragments thereof, optionally conjugated to one or more other molecules, can be used as immunogens for generating antibodies. For transmembrane molecules, such as receptors, fragments of these (e.g. the extracellular domain of a receptor) can be used as the immunogen. Optionally, the protein of interest or a fragment thereof is fused with a heterologous molecule, e.g. to form an immunoadhesin as in the examples below.

For low molecular weight antigens (such as haptens and synthetic peptides) and other antigens it may be desirable to couple the antigen with a "carrier molecule" such as serum albumin [e.g. bovine serum albumin (BSA)], ovalbumin, keyhole limpet hemacyanin (KLH), bovine thyroglobulin, soybean trypsin inhibitor or purified protein derivative of tuberculin (PPD). Such carrier molecules may be immunogenic in the animal to be immunized (i.e. they may provide class II-T-cell receptor binding sites). Coupling may be achieved using a bifunctional coupling agent, such as maleimidobenzoyl sulfosuccinimide ester (conjugation through cysteine residues), N-hydroxysuccinimide (through lysine residues), carbodiimide, glutaraldehyde, succinic anhydride, $SOCl_2$, or $R^1N=C=NR$, where R and $R^1$ are different alkyl groups. Alternatively, or in addition, the antigen and carrier molecule may be generated as a fusion protein. In general, approximately 1 mole of hapten per 50 amino acids of carrier molecule is a reasonable coupling ratio.

The antigen may be made more antigenic by coupling to large matrices, such as agarose beads; chemical coupling to cells (e.g. red blood cells); converting the antigen to larger compounds by self-polymerization (e.g. using chemical cross-linkers such as dinitrophenol or arsynyl, or by partial denaturation); preparing an immune complex; binding the antigen to nitrocellulose; and/or binding the antigen to a "carrier" protein (see above).

In another embodiment, the antigen is present in or on a cell, bacteria or virus and the host animal is immunized with the cell, bacteria or virus. Such antigen may be native to the cell, bacteria or virus or may have been introduced synthetically (e.g. by recombinant techniques, chemical coupling, etc). Preferably however, each of the antigens with which the animal is immunized has been purified by at least one purification step.

(ii) Immunization

The animal or host to be immunized with the antigens is selected. In the preferred embodiment, the animal is a rodent, e.g. a mouse.

The mouse to be immunized may, for example, be an "antigen-free" mouse as described in U.S. Pat. No. 5,721, 122, expressly incorporated herein by reference.

In one embodiment, the host is a transgenic animal in which human immunoglobulin loci have been introduced. For example, the transgenic animal may be a mouse comprising introduced human immunoglobulin genes and one in which the endogenous immunoglobulin genes have been partially or completely inactivated. Upon challenge, human antibody production in such transgenic hosts is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., *Bio/Technology* 10: 779–783 (1992); Lonberg et al., *Nature* 368:856–859 (1994); Morrison, *Nature* 368:812–13 (1994); Fishwild et al., *Nature Biotechnology* 14:845–51 (1996); Neuberger, *Nature Biotechnology* 14:826 (1996); Lonberg and Huszar, *Intern. Rev. Immunol.* 13:65–93 (1995).

The amount of each antigen administered to the host animal may, for example, range from about 0.01 μg to about 250 μg, preferably from about 0.1 μg to about 100 μg. The present invention involves immunizing the host animal with two or more different antigens, e.g. from about two to about ten different antigens, preferably from about three to about four different antigens. In the preferred embodiment of the invention, the host animal is immunized with a composition comprising a mixture of the two or more different antigens and, optionally, a physiologically acceptable diluent, such as PBS or other buffer. Alternatively, the animal can be immunized with the antigens separately. The antigens used to prepare the composition have preferably been purified by at least by one purification step.

The host animal may be immunized with the antigens in a variety of different ways. For example, by subcutaneous, intramuscular, intradermal, intravenous, and/or intraperitoneal injections. In addition, injections into lymphoid organs, popliteal lymph node and/or footpads are possible. It may be desirable to immunize the animal using a combination of two or more different administration routes, separately and/or simultaneously.

Where the primary response is weak, it may be desirable to boost the animal at spaced intervals until the antibody titer increases or plateaus. After immunization, samples of serum (test bleeds) may be taken to check the production of specific antibodies. Preferably, the host animal is given a final boost about 3–5 days prior to isolation of immune cells from the host animal.

(iii) Monoclonal antibody production

Monoclonal antibodies may be made using the hybridoma method first described by Kohler et al., *Nature*, 256:495 (1975). In the hybridoma method, "immune cells" that produce or are capable of producing polyclonal antibodies are obtained from the animal immunized as described above. Various immune cells are described above, with lymph nodes or spleen being the preferred source of immune cells for generating monoclonal antibodies. Such cells may then be fused with myeloma cells using a suitable "fusing agent", such as polyethylene glycol or Sendai virus, to form a hybridoma cell [Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and P3X63AgU.1, SP-2 or X63-Ag8-653 cells available from the American Type Culture Collection, Manassas, Va., USA. The 210-RCY3.Ag1.2.3 rat myeloma cell line is also available. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, pp. 51–63 (Marcel Dekker, Inc., New York, 1987)].

Alternatively, hybridoma cell lines may be prepared from the immune cells of the immunized animal in other ways, e.g. by immortalizing the immune cells with a virus (e.g. with Epstein Barr Virus), or with an oncogene in order to produce an immortalized cell line producing the monoclonal antibody of interest. See, also, Babcook et al. *PNAS (USA)*, 93:7843–7848 (1996), concerning production of monoclonal antibodies by cloning immunoglobulin cDNAs from single cells producing specific antibodies for yet another strategy for preparing monoclonal antibodies using immune cells of the immunized animal.

(iv) Screening

Screening is performed to identify one or more monoclonal antibodies capable of binding to each antigen. Generally, one screen for antibodies which bind to each antigen with which the animal has been immunized. Such screening may be performed on culture supernatant and/or purified antibodies, from each hybridoma culture supernatant resulting from fusion. Alternatively, or in addition, screening may be carried out using culture supernatant and/or purified antibodies from cloned hybridoma cells (see below). In addition, where cross-reactive antibodies are of interest, the ability of the monoclonal antibodies to cross-react with two or more different antigens may be determined. Moreover, it may be desirable to screen for antibodies with certain functional characteristics (e.g. agonistic activity, blocking activity, etc).

The binding specificity of monoclonal antibodies produced by hybridoma cells may, for example, be determined in an immuno-assay, e.g. by immunoprecipitation or other in vitro binding assay, such as radioimmunoassay (RIA) or enzyme-linked immunoadsorbent assay (ELISA).

There are three general classes of screening methods that can be employed (a) antibody capture assays; (b) antigen capture assays; and (c) functional screens.

In antibody capture assays, the antigen may be bound to a solid phase, monoclonal antibodies to be tested are allowed to bind to the antigen, unbound antibodies are removed by washing, and then the bound antibodies are detected, e.g. by a secondary reagent such as a labeled antibody that specifically recognizes the antibody.

For an antigen capture assay, the antigen may be labeled directly (various labels are described herein). In one embodiment, monoclonal antibodies to be tested may be bound to a solid phase and then reacted with the optionally labeled antigen. Alternatively, the antibody-antigen complex may be allowed to form by immunoprecipitation prior to binding of the monoclonal antibody to be tested to a solid phase. Once the antibody-antigen complexes are bound to the solid phase, unbound antigen may be removed by washing and positives may be identified by detecting the antigen.

Various functional screens exist for identifying monoclonal antibodies with desired activities. Examples include the agonistic activity assay and blocking assay of the examples below; keratinocyte monolayer adhesion assay and the mixed lymphocyte response (MLR) assay [Werther et al. *J. Immunol.* 157:4986–4995 (1996)]; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and hematopoiesis assays (see WO 95/27062). The class/subclass of the antibodies may be determined, e.g., by double-diffusion assays; antibody capture on antigen-coated plates; and/or antibody capture on anti-IgG antibodies.

To screen for antibodies which bind to a particular epitope on the antigen of interest (e.g., those which block binding of any of the antibodies disclosed herein to an Apo-2L receptor), a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388–1394 (1995), can be performed to determine whether the antibody binds an epitope of interest.

After hybridoma cells are identified that produce antibodies of the desired specificity, affinity, and/or activity, single-cell clones may be subcloned by limiting dilution procedures [Goding, *Monoclonal Antibodies: Principles and Practice*, pp.59–103 (Academic Press, 1986)]; single cell cloning by picks; or cloning by growth in soft agar [Harlow and Lane, *Antibodies: A Laboratory Manual* Cold Spring Harbor Laboratory (1988); pps 224–227].

Hybridoma clones may be grown by standard methods. Suitable culture media for this purpose include, for example, DMEM or RPMI-1640 medium. In addition, the hybridoma cells may be grown in vivo as ascites tumors in an animal. [Harlow and Lane, *Antibodies: A Laboratory Manual* Cold Spring Harbor Laboratory (1988); Chapter 7].

The monoclonal antibodies secreted by the subclones are suitably separated from the culture medium, ascites fluid, or serum by conventional immunoglobulin purification procedures such as, for example, protein G or A-Sepharose, hydroxylapatite chromatography, gel electrophoresis, dialysis, or affinity chromatography.

(v) Cloning and further modifications of the MAb

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

The DNA also may be modified, for example, by substituting the coding sequence for human heavy- and light-chain constant domains in place of the homologous murine sequences [U.S. Pat. No. 4,816,567; Morrison, et al., *Proc. Natl Acad. Sci. USA*, 81:6851 (1984)], or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In one embodiment, the monoclonal antibody is humanized. Humanized forms of non-human (e.g., murine) antibodies are chimeric immunoglobulins, immunoglobulin chains or fragments thereof [such as Fv, Fab, Fab', F(ab')$_2$ or other antigen-binding subsequences of antibodies] which contain minimal sequence derived from non-human immunoglobulin. A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody [Sims et al., *J. Immunol.*, 151:2296 (1993); Chothia et al., *J. Mol. Biol.*, 196:901 (1987)]. Another method uses a particular framework derived from the consensus sequence of all human antibodies of a particular subgroup of light or heavy chains. The same framework may be used for several-different humanized antibodies [Carter et al., *Proc. Natl. Acad. Sci. USA*, 89:4285 (1992); Presta et al., *J. Immnol.*, 151:2623 (1993)].

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The antibodies of the invention may also be prepared as monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab')$_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'—SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

It may be desirable to generate a multispecific antibody comprising the monoclonal antibody. Multispecific antibodies have binding specificities for at least two different antigens. While such molecules normally will only bind two antigen (i.e. bispecific antibodies, BsAbs), antibodies with additional specificities such as trispecific antibodies are encompassed by this expression when used herein. Bispecific antibodies can be prepared as full length antibodies or antibody fragments [e.g. F(ab')$_2$ bispecific antibodies].

Methods for making bispecific antibodies are known in the art. Traditional production of full length bispecific antibodies is based on the coexpression of two immunoglobulin heavy chain-light chain pairs, where the two chains have different specificities [Millstein et al., *Nature*, 305:537–539 (1983)]. Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this symmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies are contemplated. For example, trispecific antibodies can be prepared. Tutt et al. *J. Immunol.* 147: 60 (1991).

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugate antibodies. Examples include $^{212}$Bi, $^{131}$I, $^{90}$Y, $^{186}$Re.

Conjugates of the antibody and cytotoxic agent may be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science*, 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Immunoliposomes comprising the antibody may also be prepared. Liposomes containing the antibody are prepared by methods known in the art, such as described in Epstein et al., *Proc. Natl. Acad. Sci. USA*, 82:3688 (1985); Hwang et al., *Proc. Natl Acad. Sci. USA*, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286–288 (1982) via a disulfide interchange reaction. A chemotherapeutic agent (such as Doxorubicin) is optionally contained within the liposome. See Gabizon et al. *J. National Cancer Inst.* 81(19):1484 (1989).

The antibody of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs [see, e.g., Massey, Nature 328: 457–458 (1987)]. Antibody-abzyme conjugates can be prepared as described herein for delivery of the abzyme to a tumor cell population.

The enzymes of this invention can be covalently bound to the antibody by techniques well known in the art such as the use of the heterobifunctional crosslinking reagents discussed above. Alternatively, fusion proteins comprising at least the antigen-binding region of an antibody of the invention linked to at least a functionally active portion of an enzyme of the invention can be constructed using recombinant DNA techniques well known in the art [see, e.g., Neuberger et al., *Nature*, 312: 604–608 (1984)].

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment. See, e.g., U.S. Pat. No. 5,747,035, expressly incorporated herein by reference.

Covalent modifications of the antibody are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

The antibodies may optionally be covalently attached or conjugated to one or more chemical groups. A polyol, for example, can be conjugated to an antibody molecule at one or more amino acid residues, including lysine residues as disclosed in WO 93/00109. Optionally, the polyol is a poly(alkelene glycol), such as poly(ethylene glycol) (PEG), however, those skilled in the art recognize that other polyols, such as, for example, poly(propylene glycol) and polyethylene-polypropylene glycol copolymers, can be employed using techniques for conjugating PEG to polypeptides. A variety of methods for pegylating polypeptides have been described. See, e.g. U.S. Pat. No. 4,179,337 which discloses the conjugation of a number of hormones and enzymes to PEG and polypropylene glycol to produce physiologically active compositions having reduced immunogenicities.

The antibodies may also be fused or linked to another heterologous polypeptide or amino acid sequence such as an epitope tag.

B. Anti-Apo-2L Receptor Antibodies

The present also provides antibodies which are able to cross-react with two or more different Apo-2L receptors. These cross-reactive antibodies may be prepared according to the mixed antigen immunization method described above (or by immunizing an animal with a single antigen, e.g. Apo-2 or another Apo-2L receptor), or may be made by other techniques such as those elaborated below.

As described in the Examples below, anti-Apo-2 monoclonal antibodies have been prepared. Three of these antibodies (3H1.18.10, 3H3.14.5 and 3D5.1.10) have been deposited with the ATCC. In one embodiment, the monoclonal antibodies of the invention will have the same biological characteristics as one or more of the monoclonal antibodies secreted by the three hybridoma cell lines deposited with the ATCC producing antibodies 3H1.18.10, 3H3.14.5 or 3D5.1.10. The term "biological characteristics" is used to refer to the in vitro and/or in vivo activities or properties of the monoclonal antibody, such as the ability to specifically bind to Apo-2 and/or another Apo-2L receptor, or to substantially block, induce or enhance Apo-2L receptor activation. Optionally, the monoclonal antibody will bind to the same epitope as one or more of the 3H1.18.10, 3H3.14.5 or 3D5.1.10 antibodies disclosed herein. The monoclonal antibody preferably has the hypervariable region residues of one or more of the above-mentioned antibodies, e.g., it may comprise a humanized variant.

Aside from the methods described above for obtaining antibodies (by immunizing a host with one or more antigens), other techniques are available for generating anti-Apo-2L receptor antibodies. For example, human antibodies can be produced in phage display libraries [Hoogenboom and Winter, *J. Mol. Biol.*, 227:381 (1992); Marks et al., *J. Mol. Biol.*, 222:581 (1991)]. The techniques of Cole et al. and Boerner et al. are also available for the preparation of human monoclonal antibodies [Cole et al., *Monoclonal Antibodies and Cancer Therapy*, Alan R. Liss, p. 77 (1985) and Boerner et al., *J. Immunol.*, 147(1):86–95 (1991)]. Suitable methods for preparing phage libraries have been reviewed and are described in Winter et al., *Annu. Rev. Immunol.*, 12:433–55 (1994); Soderlind et al., *Immunological Reviews*, 130:109–123 (1992); Hoogenboom, *Tibtech* February 1997, Vol. 15; Neri et al., *Cell Biophysics*, 27:47–61 (1995). Libraries of single chain antibodies may also be prepared by the methods described in WO 92/01047, WO 92/20791, WO 93/06213, WO 93/11236, WO 93/19172, WO 95/01438 and WO 95/15388. Antibody libraries are also commercially available, for example, from Cambridge Antibody Technologies (C.A.T.), Cambridge, UK.

C. Recombinant Antibodies

The invention also provides isolated nucleic acid encoding an antibody as disclosed herein (e.g. as obtained by mixed antigen immunization and/or an anti-Apo-2L receptor antibody), vectors and host cells comprising the nucleic acid, and recombinant techniques for the production of such antibodies.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. Examples of such expression system components are disclosed in U.S. Pat. No. 5,739,277 issued Apr. 14, 1998, expressly incorporated herein by reference.

Suitable host cells for cloning or expressing the DNA in the vectors herein are the prokaryote, yeast, or higher eukaryote cells (see, e.g., U.S. Pat. No. 5,739,277, expressly incorporated herein by reference.)

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce the antibody of this invention may be cultured in a variety of media. Any necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma1$, $\gamma2$, or $\gamma4$ heavy chains (Lindmark et al., *J. Immunol. Meth.* 62:1–13 (1983)). Protein G is recommended for all mouse isotypes and for human $\gamma3$ (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

D. Therapeutic Uses for Antibodies

The antibodies described herein have therapeutic utility. Agonistic Apo-2L receptor antibodies, for instance, may be employed to activate or stimulate apoptosis in cancer cells. Accordingly, the invention provides methods for treating cancer using antibodies, such as cross-reactive Apo-2L receptor antibodies. It is of course contemplated that the methods of the invention can be employed in combination with still other therapeutic techniques such as surgery.

The antibody is preferably administered to the mammal in a carrier. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of a pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibody can be administered to the mammal by injection (e.g., intravenous, intraperitoneal, subcutaneous, intramuscular), or by other methods such as infusion that ensure its delivery to the bloodstream in an effective form. The antibody may also be administered by intratumoral, peritumoral, intralesional, or perilesional routes, to exert local as well as systemic therapeutic effects. Local or intravenous injection is preferred.

Effective dosages and schedules for administering the antibody may be determined empirically, and making such determinations is within the skill in the art. Those skilled in the art will understand that the dosage of antibody that must be administered will vary depending on, for example, the mammal which will receive the antibody, the route of administration, the particular type of antibody used and other drugs being administered to the mammal. Guidance in selecting appropriate doses for antibody is found in the literature on therapeutic uses of antibodies, e.g., *Handbook of Monoclonal Antibodies*, Ferrone et al., eds., Noges Publications, Park Ridge, N.J., (1985) ch. 22 and pp. 303–357; Smith et al., *Antibodies in Human Diagnosis and Therapy*, Haber et al., eds., Raven Press, New York (1977) pp. 365–389. A typical daily dosage of the antibody used alone might range from about 1 µg/kg to up to 100 mg/kg of body weight or more per day, depending on the factors mentioned above.

The antibody may also be administered to the mammal in combination with effective amounts of one or more other therapeutic agents or in conjunction with radiation treatment. Therapeutic agents contemplated include chemotherapeutics as well as immunoadjuvants and cytokines. The antibody may be administered sequentially or concurrently with the one or more other therapeutic agents. The amounts of antibody and therapeutic agent depend, for example, on what type of drugs are used, the cancer being treated, and the scheduling and routes of administration but would generally be less than if each were used individually.

Following administration of antibody to the mammal, the mammal's cancer and physiological condition can be monitored in various ways well known to the skilled practitioner. For instance, tumor mass may be observed physically or by standard x-ray imaging techniques.

The Apo-2L receptor antibodies of the invention may also be useful in enhancing immune-mediated cell death in cells expressing Apo-2L receptor(s), for instance, through complement fixation or ADCC. Alternatively, antagonistic anti-Apo-2L receptor antibodies may be used to block excessive apoptosis (for instance in neurodegenerative disease) or to block potential autoimmune/inflammatory effects of Apo-2 resulting from NF-κB activation. Such antagonistic antibodies can be utilized according to the therapeutic methods and techniques described above.

E. Non-therapeutic Uses for Antibodies

Antibodies may further be used in diagnostic assays for their antigen, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Technicrues*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Antibodies also are useful for the affinity purification of antigen from recombinant cell culture or natural sources. In this process, the antibodies are immobilized on a suitable support, such as Sephadex resin or filter paper, using methods well known in the art. The immobilized antibody then is contacted with a sample containing the antigen to be purified, and thereafter the support is washed with a suitable solvent that will remove substantially all the material in the sample except the antigen, which is bound to the immobilized antibody. Finally, the support is washed with another suitable solvent that will release the antigen from the antibody.

F. Kits Containing Antibodies

In a further embodiment of the invention, there are provided articles of manufacture and kits containing antibodies which can be used, for instance, for the therapeutic or non-therapeutic applications described above. The article of manufacture comprises a container with a label. Suitable containers include, for example, bottles, vials, and test tubes. The containers may be formed from a variety of materials such as glass or plastic. The container holds a composition which includes an active agent that is effective for therapeutic or non-therapeutic applications, such as described above. The active agent in the composition is the antibody, e.g. an Apo-2L receptor antibody. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLE 1

Preparation of Immunogens

The receptor antigens in Examples 2 and 3 below were all receptors for Apo-2 ligand [Pitti et al., *J. Biol. Chem.*, 271:12687–12690 (1996); and WO97/25428]. The Apo-2L receptors were: DR4 [Pan et al., *Science*, 276:111–113 (1997)]; Apo-2 (called "DR5" in Sheridan et al., *Science* 277:818–821 (1997)]; DcR1 [Sheridan et al., *Science* 277:818–821 (1997)]; and DcR2 [Marsters et al., *Curr. Biol.*, 7:1003–1006 (1997)].

Receptor immunoadhesins (designated "DR4-IgG", "Apo-2-IgG", "DcR1-IgG" and "DcR2-IgG") were prepared by fusing the extracellular domain sequence of each receptor to the hinge and Fc region of human immunoglobulin $G_1$ heavy chain in pRK5 as described previously [Ashkenazi et al., *Proc. Natl. Acad. Sci.*, 88:10535–10539 (1991)]. The immunoadhesin proteins were expressed by transient transfection into human 293 cells and purified from cell supernatants by protein A affinity chromatography, as described by Ashkenazi et al., supra. Purified immunoadhesin was suspended in phosphate buffered saline (PBS).

EXAMPLE 2

Mixed Antigen Immunization

Animals in this example were immunized with the four receptor immunoadhesins of the preceding example. The mixed antigen immunization scheme used is shown in FIG. 1.

Balb/c mice (obtained from Charles River Laboratories) were immunized into each hind foot pad 14 times at 3–4 day intervals, with a mixture of DR4-IgG, Apo-2-IgG, DcR1-IgG and DcR2-IgG (1 µg each) suspended in monophosphoryl lipid A plus trehalose dicorynomycolate adjuvant (MPL-TDM; Ribi Immunochem. Research Inc., Hamilton, Mont.) at a 1:1 ratio of immunoadhesin:adjuvant (DcR2-IgG was only included in the mixture used for the final six immunizations).

Three days after the final boost, popliteal lymph node cells nodes were removed from the mice and a single cell suspension was prepared in DMEM media (obtained from Biowhitakker Corp.) supplemented with 1% penicillin-streptomycin. The lymph node cells were fused with murine myeloma cells P3X63AgU.1 (ATCC CRL 1597) using 35% polyethylene glycol and cultured in 96-well culture plates.

Hybridomas were selected in super DMEM [DMEM plus 10% fetal calf serum (FCS), 10% NCTC-109 (BioWittaker, Wakersville, Md.), 100 mM pyruvate, 100 U/ml insulin, 100 mM oxaloacetic acid, 2 mM glutamine, 1% nonessential amino acids (GIBCO), 100 U/ml penicillin and 100 µg/ml streptomycin] containing 100 µM hypoxanthine, 0.4 µM aminopterin, and 16 µM thymidine (1×HAT, Sigma Chemical Co., St. Louis, Mo.).

Ten days after the fusion, 180 µl of each hybridoma culture supernatant was screened for the presence of antibodies to three different antigens (i.e. DR4-IgG, Apo-2-IgG and CD4-IgG control) in a capture ELISA. Hybridoma cells were re-fed with 200 µl of super DMEM containing 10% FCS and antibiotics. Two days later, 180 µl of culture supernatant was collected and screened for the presence of antibodies to another two different antigens (i.e. DcR1-IgG and DcR2-IgG) in a capture ELISA. After careful examination of the ELISA results, potential positive hybridomas secreting monoclonal antibodies against each antigen were cloned twice using a limiting dilution method. Culture supernatants from these clones were re-tested for their ability to bind to a particular antigen, but not to others, including CD4-IgG, in a capture ELISA. Isotypes of the antibodies were also determined.

Selected clones were also tested for (a) their ability to recognize Apo-2L receptors expressed on cell membranes by flow cytometry (FACS); (b) their ability to block the ligand-receptor interaction, and (c) for their agonistic activity.

EXAMPLE 3

Single Antigen Immunization

The single antigen immunization scheme is shown in FIG. 2. The general method was almost the same as the mixed antigen immunization protocol in Example 2 above, except that only a single antigen was used as the immunogen and during the screening of hybridomas supernatant (180 µl) was collected only once to screen for the presence of positive monoclonal antibodies to the particular antigen and control CD4-IgG.

Balbic mice (obtained from Charles River Laboratories) were immunized by injecting 0.5 µg/50 µl of immunoadhesin protein (diluted in MPL-TDM adjuvant purchased from Ribi Immunochemical Research Inc., Hamilton, Mont.) 10 times into each hind foot pad at 3–4 day intervals. Three days after the final boost, popliteal lymph nodes were removed from the mice and a single cell suspension was prepared in DMEM media (obtained from Biowhitakker Corp.) supplemented with 1% penicillin-streptomycin. The lymph node cells were then fused with murine myeloma cells P3X63AgU.1 (ATCC CRL 1597) using 35% polyethylene glycol and cultured in 96-well culture plates. Hybridomas resulting from the fusion were selected in HAT medium as in Example 2. Ten days after the fusion, hybridoma culture supernatants (180 µl) were screened in an ELISA to test for the presence of monoclonal antibodies binding to the immunoadhesin protein.

EXAMPLE 4

Capture ELISA

For the capture ELISA, 96-well microtiter plates (Maxisorb; Nunc, Kamstrup, Denmark) were coated by adding 50 µl of 2 µg/ml goat anti-human IgG Fc (purchased from Cappel Laboratories) in PBS to each well and incubating at 4° C. overnight. The plates were then washed three times with wash buffer (PBS containing 0.05% TWEEN 20™). The wells in the microtiter plates were then blocked with 50 µl of 2.0% bovine serum albumin (BSA) in PBS and incubated at room temperature for 1 hour. The plates were then washed again three times with wash buffer.

After the washing step, 50 µl of 1 µg/ml immunoadhesin protein (as described above) in assay buffer (PBS plus 0.5% BSA) was added to each well. The plates were incubated for 1 hour at room temperature on a shaker apparatus, followed by washing three times with wash buffer.

Following the wash steps, 100 µl of the hybridoma supernatants or purified antibody (using Protein G-sepharose columns) (1 µg/ml) was added to designated wells. 100 µl of P3X63AgU.1 myeloma cell conditioned medium was added to other designated wells as controls. The plates were incubated at room temperature for 1 hour on a shaker apparatus and then washed three times with wash buffer.

Next, 50 µl HRP-conjugated goat anti-mouse IgG Fc (purchased from Cappel Laboratories), diluted 1:1000 in assay buffer (0.5% bovine serum albumin, 0.05% % TWEEN 20™, 0.01% Thimersol in PBS), was added to each well and the plates incubated for 1 hour at room temperature on a shaker apparatus. The plates were washed three times with wash buffer, followed by addition of 50 µl of substrate (TMB microwell peroxidase substrate, Kirkegaard & Perry, Gaithersburg, Md.) to each well and incubation at room temperature for 10 minutes. The reaction was stopped by adding 50 μl of TMB 1-component stop solution (diethyl glycol, Kirkegaard & Perry) to each well, and absorbance at 450 nm was read in an automated microtiter plate reader.

EXAMPLE 5

Antibody Isotyping

The isotypes of antibodies were determined by coating microtiter plates with isotype specific goat anti-mouse Ig (Fisher Biotech, Pittsburgh, Pa.) overnight at 4° C. The plates were then washed with wash buffer. The wells in the microtiter plates were then blocked with 200 μl of 2% bovine serum albumin and incubated at room temperature for one hour. The plates were washed again three times with wash buffer. Next, 100 μl of hybridoma culture supernatant or 5 μg/ml of purified antibody was added to designated wells. The plates were incubated at room temperature for 30 minutes and then 50 μl HRP-conjugated goat anti-mouse IgG (as described above) was added to each well. The plates were incubated for 30 minutes at room temperature. The level of HRP bound to the plate was detected using HRP substrate as described above.

EXAMPLE 6

Flow Cytometry

FACS analysis was performed using 9D cells (a human B lymphoid cell line expressing Apo-2 and DR4; Genentech, Inc.) or human microvascular endothelial (HUMEC) cells (Cell Systems, Inc.), expressing DcR1 and DcR2.

Twenty-five microliters of cell suspension (4×10$^6$ cells/ml) in cell sorter buffer (PBS containing 1% FCS and 0.02% NaN$_3$) was added to U-bottom microtiter wells, mixed with 100 μl of culture supernatant or purified monoclonal antibody (purified on Protein-G sepharose column) (10 μg/ml) in cell sorter buffer (CSB), and incubated for 30 min on ice. After washing, cells were incubated with 100 μl of FITC-conjugated goat anti-mouse IgG for 30 min at 4° C. Cells were washed twice in CSB and resuspended in 150 μl of CSB and analyzed by FACScan (Becton Dickinson, Mountain View, Calif.).

EXAMPLE 7

Assay for Antibody Ability to Block Apo-2L-induced Apoptosis

Hybridoma supernatants and purified antibodies were tested for their ability to block Apo-2 ligand induced 9D cell apoptosis. Human 9D cells (5×10$^5$ cells) were suspended in 50 μl of complete RPMI medium (RPMI plus 10% FCS, glutamine, nonessential amino acid, penicillin and streptomycin and sodium pyrubate) in Falcon 2052 tubes. 10 μg of antibody plus 10 μg of DR4 antibody in 200 μl of medium was added to cells and cells were incubated on ice for 15 minutes. 0.5 μg of Apo-2L (soluble His-tagged Apo-2L prepared as described in WO 97/25428; see also Pitti et al., supra) in 250 μl of complete RPMI was added to cells. 9D cells were incubated overnight at 37° C. in the presence of 7% CO$_2$. Cells were harvested and washed once in PBS. The viability of the cells was then determined by the staining of FITC-Annexin V binding to phosphatidylserine according to manufacturer's recommendations (Clontech). Briefly cells washed in PBS were resuspended in 200 μl of binding buffer. Ten μl of Annexin V-FITC (1 μg/ml) and 10 μl of propidium iodide were added to the cells. After incubation for 15 min in the dark, cells were analyzed by FACScan.

EXAMPLE 8

Apoptosis by Monoclonal Antibodies After Crosslinking with Anti-mouse Ig

Human 9D cells (2.5×10$^5$ cells) in 50 μl of complete RPMI medium (RPMI plus 10% FCS, glutamine, nonessential amino acid, penicillin and streptomycin and sodium pyruvate) were added to Falcon 2052 tubes. Cells were then incubated with 1 μg of monoclonal antibody in 100 μl of complete RPMI medium on ice for 15 min. Cells were then incubated with 10 μg of goat anti-mouse IgG Fc in 350 μl of complete RPMI medium overnight at 37° C. After washing once with PBS, cells were resuspended in 200 μl of PBS containing 0.5% BSA and incubated with 10 μl of FITC-Annexin and 10 μl of propidium iodide for 15 min in the dark. Dead cells then detected by FACScan as described above.

RESULTS AND DISCUSSION

FIGS. 3 and 4 provide a comparison of the antigen specific sera titer from mice immunized with a single antigen (FIG. 3) verses mice immunized with mixed antigens (FIG. 4).

Sera titers (EC50) from mice immunized with each antigen were approximately 10,000 for each specific antigen. Antigen specific sera titers (EC50) of mice immunized with mixed antigens were ~10,000 for DR4-IgG, Apo-2-IgG, DcR1-IgG and ~5,000 for DcR2-IgG. Accordingly, the antigen specific antibody titers were quite comparable whether mice were immunized with individual antigen or with a mixture of four different antigens. The DcR2-IgG specific titer (~1:4,000) of mice immunized with four different antigens was slightly lower than that (~1:10,000) of mice immunized with DcR2-IgG alone. However, this may have been due to the fact that the mice immunized with mixed antigens received DcR2-IgG only 6 times, while mice immunized with DcR2-IgG alone received 10 injections.

TABLE 1

COMPARISON BETWEEN SINGLE ANTIGEN AND MIXED ANTIGEN IMMUNIZATIONS

|  | DR4 | | Apo-2 | | DcR2 | |
| --- | --- | --- | --- | --- | --- | --- |
|  | Single Antigen | Mixed Antigen | Single Antigen | Mixed Antigen | Single Antigen | Mixed Antigen |
| ELISA Positive | 13.30% | 6.50% | 4.50% | 2.10% | 1.20% | 2.30% |
| FACS Positive | 48% | 17% | 36% | 46% | 20% | 0 |
| Final monoclonal antibody selected | 5 | 3 | 4 | 5 | 1 | 0 |
| Specificity | 3/5 | 1/3 | 1/4 | 1/5 | | |
| Cross-Reactive* | 0/5 | 1/3 | 0/4 | 1/5 | | |

*Specifically cross-react with both DR4 and Apo-2

Table 1 compares the effectiveness of generating monoclonal antibodies to DR4, Apo-2 and DcR2 using mice immunized with a single antigen, verses mice immunized with mixed antigens. One can generate monoclonal antibodies using both methods. However, the mixed antigen immunization scheme resulted in the production and isolation of more antibodies that cross-reacted with different receptors (i.e., recognized shared epitopes between two proteins; see Table 1). In particular, using the mixed antigen immunization protocol, antibodies were identified which cross-reacted with different Apo-2L receptors. The cross-reactivities as determined by capture ELISA are shown in Table 2.

TABLE 2

ANTIBODY CROSS-REACTIVITIES WITH APO-2L RECEPTORS

| | | Cross Reactivity | | | |
|---|---|---|---|---|---|
| | Isotype | DR4 | Apo-2 | DcR1 | DcR2 |
| 3H1.18.10 | G1 | +/− | +++ | +/− | +/− |
| 3H3.14.5 | G1 | +/− | +++ | +/− | +/− |
| 3D5.1.10 | G1 | ++ | +++ | − | +/− |

++ ≧75% binding (compared to Apo-2 binding)
+ ~50–74% binding
+/− ~25–49% binding
− ≦24% binding As shown in FIG. 6C and Table 2, the 3D5.1.10 antibody specifically bound Apo-2 and specifically cross-reacted with DR4. Antibodies 3H1.18.10 and 3H3.14.5 specifically bound Apo-2 and displayed some cross-reactivity with other Apo-2L receptors tested. (Table 2 and FIGS. 6A and 6B) Other biological activities of the antibodies from Table 2 were evaluated according to the methods described in Example 6 (antibody binding to cell-surface receptor); Example 7 (blocking or neutralizing ability); and Example 8 (apoptotic activity). The results are shown in Table 3 below.

TABLE 3

OTHER ACTIVITIES OF
THE ANTI-APO-2L RECEPTOR ANTIBODIES

| | FACS of 9D cells | Blocking ability | Apoptotic activity |
|---|---|---|---|
| 3H1.18.10 | + | − | − |
| 3H3.14.5 | + | + | + |
| 3D5.1.10 | + | − | − |

All three antibodies were able to bind Apo-2 expressed on the surface of 9D cells. The 3H3.14.5 antibody was also able to inhibit apoptosis induced via interaction between Apo-2L and Apo-2. This antibody was further capable of inducing apoptosis of 9D cells in the presence of an anti-Fc antibody to cross-link antibodies.

Deposit of Material

The following materials have been deposited with the American Type Culture Collection, 1801 Universal Blvd., ssas, Va., USA (ATCC):

| Material | ATCC Dep. No. | Deposit Date |
|---|---|---|
| pRK5-Apo-2 | 209021 | May 8, 1997 |
| 3F11.39.7 | HB-12456 | Jan 13, 1998 |
| 3H1.18.10 | HB-12535 | June 2, 1998 |
| 3H3.14.5 | HB-12534 | June 2, 1998 |
| 3D5.1.10 | HB-12536 | June 2, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated antibody which specifically cross-reacts with two or more different Apo-2L receptors.

2. The antibody of claim 1 comprising a monoclonal antibody.

3. The antibody of claim 1 which specifically binds to Apo-2 polypeptide and further specifically cross-reacts with another Apo-2L receptor.

4. The antibody of claim 1, which specifically binds to Apo-2 polypeptide and further specifically cross-reacts with DR4.

5. The antibody of claim 1 which is an agonistic antibody.

6. A method of inducing apoptosis in mammalian cancer cells comprising exposing mammalian cancer cells to an effective amount of the agonistic antibody of claim 5.

7. The method of claim 6 wherein the agonistic antibody binds to Apo-2 polypeptide or DR4.

8. The antibody of claim 1 which is a blocking antibody.

9. The antibody of claim 1 which is an antibody fragment.

10. The antibody of claim 1 which comprises non-human hypervariable region residues and human framework region residues.

11. The antibody of claim 1 which is a human antibody.

12. A composition comprising the antibody of claim 1 and a pharmaceutically acceptable carrier.

13. An article of manufacture comprising a container and a composition contained within said container, wherein the composition includes the antibody of claim 1.

14. The article of manufacture of claim 13 further comprising instructions for using the antibody in vivo or ex vivo.

15. The antibody of claim 1 wherein the Apo-2L receptors are native sequence Apo-2L receptors.

16. An antibody having the biological characteristics of a monoclonal antibody selected from the group consisting of 3H1.18.10 (produced by the hybridoma having ATCC Accession No. HB-12535), 3H3.14.5 (produced by the hybridoma having ATCC Accession No. HB-12534) and 3D5.1.10 (produced by the hybridoma having ATCC Accession No. HB-12536).

17. The antibody of claim 16 which binds to the same epitope as the epitope to which a monoclonal antibody selected from the group consisting of 3H1.18.10 (produced by the hybridoma having ATCC Accession No. HB-12535), 3H3.14.5 (produced by the hybridoma having ATCC Accession No. HB-12534) and 3D5.1.10 (produced by the hybridoma having ATCC Accession No. HB-12536) binds.

18. The monoclonal antibody of claim which has the hypervariable region residues of a monoclonal antibody selected from the group consisting of 3H1.18.10 (produced by the hybridoma having ATCC Accession No. HB-12535), 3H3.14.5 (produced by the hybridoma having ATCC Accession No. HB-12534) and 3D5.1.10(produced by the hybridoma having ATCC Accession No. HB-12536).

19. A hybridoma cell line which produces a monoclonal antibody selected from the group consisting of 3H1.18.10 (produced by the hybridoma having ATCC Accession No. HB-12535), 3H3.14.5 (produced by the hybridoma having ATCC Accession No. HB-12534) and 3D5.1.10 (produced by the hybridoma having ATCC Accession No. HB-12536).

* * * * *

UNITED STATES PATENT AND TRADEMARK OFFICE
CERTIFICATE OF CORRECTION

PATENT NO. : 6,252,050 B1
DATED : June 26, 2001
INVENTOR(S) : Ashkenazi et al.

It is certified that error appears in the above-identified patent and that said Letters Patent is hereby corrected as shown below:

<u>Column 38, claim 18,</u>
Line 31, please insert -- 16 -- after "claim".

Signed and Sealed this

Sixteenth Day of April, 2002

Attest:

JAMES E. ROGAN
*Attesting Officer*     *Director of the United States Patent and Trademark Office*

SEQUENCE LISTING

<160> NUMBER OF SEQ ID NOS: 2

<210> SEQ ID NO 1
<211> LENGTH: 1799
<212> TYPE: DNA
<213> ORGANISM: human

-continued

```
<400> SEQUENCE: 1
cccacgcgtc cgcataaatc agcacgcggc cggagaaccc cgcaatctct         50
gcgcccacaa aatacaccga cgatgcccga tctactttaa gggctgaaac        100
ccacgggcct gagagactat aagagcgttc cctaccgcca tggaacaacg        150
gggacagaac gccccggccg cttcggggcc cggaaaagg cacggcccag         200 gacccaggga ggcgcgggga gccaggcctg ggctccgggt ccccaagacc        250
cttgtgctcg ttgtcgccgc ggtcctgctg ttggtctcag ctgagtctgc        300
tctgatcacc caacaagacc tagctcccca gcagagagcg gccccacaac        350
aaaagaggtc cagcccctca gagggattgt gtccacctgg acaccatatc        400
tcagaagacg gtagagattg catctcctgc aaatatggac aggactatag        450
cactcactgg aatgacctcc ttttctgctt gcgctgcacc aggtgtgatt        500
caggtgaagt ggagctaagt ccctgcacca cgaccagaaa cacagtgtgt        550
cagtgcgaag aaggcacctt ccgggaagaa gattctcctg agatgtgccg        600
gaagtgccgc acagggtgtc ccagagggat ggtcaaggtc ggtgattgta        650
caccctggag tgacatcgaa tgtgtccaca aagaatcagg catcatcata        700
ggagtcacag ttgcagccgt agtcttgatt gtggctgtgt ttgtttgcaa        750
gtctttactg tggaagaaag tccttcctta cctgaaaggc atctgctcag        800
gtggtggtgg ggaccctgag cgtgtggaca gaagctcaca acgacctggg        850
gctgaggaca atgtcctcaa tgagatcgtg agtatcttgc agcccaccca        900
ggtccctgag caggaaatgg aagtccagga gccagcagag ccaacaggtg        950
tcaacatgtt gtcccccggg gagtcagagc atctgctgga accggcagaa       1000
gctgaaaggt ctcagaggag gaggctgctg gttccagcaa atgaaggtga       1050
tcccactgag actctgagac agtgcttcga tgactttgca gacttggtgc       1100
cctttgactc ctgggagccg ctcatgagga agttgggcct catggacaat       1150
gagataaagg tggctaaagc tgaggcagcg ggccacaggg acaccttgta       1200
cacgatgctg ataaagtggg tcaacaaaac cgggcgagat gcctctgtcc       1250
acaccctgct ggatgccttg gagacgctgg gagagagact tgccaagcag       1300
aagattgagg accacttgtt gagctctgga aagttcatgt atctagaagg       1350
taatgcagac tctgccwtgt cctaagtgtg attctcttca ggaagtgaga       1400
ccttccctgg tttacctttt ttctggaaaa agcccaactg gactccagtc       1450
agtaggaaag tgccacaatt gtcacatgac cggtactgga agaaactctc       1500
ccatccaaca tcacccagtg gatggaacat cctgtaactt tcactgcac        1550 ttggcattat tttataagc tgaatgtgat aataaggaca ctatggaaat         1600
gtctggatca ttccgtttgt gcgtactttg agatttggtt tgggatgtca       1650
ttgttttcac agcactttt tatcctaatg taaatgcttt atttatttat        1700
ttgggctaca ttgtaagatc catctacaaa aaaaaaaaa aaaaaaaag          1750 ggcggccgcg actctagagt cgacctgcag aagcttggcc gccatggcc         1799

<210> SEQ ID NO 2
<211> LENGTH: 411
<212> TYPE: PRT
<213> ORGANISM: human
```

```
<220> FEATURE:
<221> NAME/KEY: xaa
<222> LOCATION: 410
<223> OTHER INFORMATION: xaa = leu or met

<400> SEQUENCE: 2

Met Glu Gln Arg Gly Gln Asn Ala Pro Ala Ser Gly Ala Arg
 1               5                  10                  15

Lys Arg His Gly Pro Gly Pro Arg Glu Ala Arg Gly Ala Arg Pro
                20                  25                  30

Gly Leu Arg Val Pro Lys Thr Leu Val Leu Val Val Ala Ala Val
                35                  40                  45

Leu Leu Leu Val Ser Ala Glu Ser Ala Leu Ile Thr Gln Gln Asp
                50                  55                  60

Leu Ala Pro Gln Gln Arg Ala Ala Pro Gln Gln Lys Arg Ser Ser
                65                  70                  75

Pro Ser Glu Gly Leu Cys Pro Pro Gly His His Ile Ser Glu Asp
                80                  85                  90

Gly Arg Asp Cys Ile Ser Cys Lys Tyr Gly Gln Asp Tyr Ser Thr
                95                 100                 105

His Trp Asn Asp Leu Leu Phe Cys Leu Arg Cys Thr Arg Cys Asp
               110                 115                 120

Ser Gly Glu Val Glu Leu Ser Pro Cys Thr Thr Thr Arg Asn Thr
               125                 130                 135

Val Cys Gln Cys Glu Glu Gly Thr Phe Arg Glu Glu Asp Ser Pro
               140                 145                 150

Glu Met Cys Arg Lys Cys Arg Thr Gly Cys Pro Arg Gly Met Val
               155                 160                 165

Lys Val Gly Asp Cys Thr Pro Trp Ser Asp Ile Glu Cys Val His
               170                 175                 180

Lys Glu Ser Gly Ile Ile Gly Val Thr Val Ala Ala Val Val
               185                 190                 195

Leu Ile Val Ala Val Phe Val Cys Lys Ser Leu Leu Trp Lys Lys
               200                 205                 210

Val Leu Pro Tyr Leu Lys Gly Ile Cys Ser Gly Gly Gly Gly Asp
               215                 220                 225

Pro Glu Arg Val Asp Arg Ser Ser Gln Arg Pro Gly Ala Glu Asp
               230                 235                 240

Asn Val Leu Asn Glu Ile Val Ser Ile Leu Gln Pro Thr Gln Val
               245                 250                 255

Pro Glu Gln Glu Met Glu Val Gln Glu Pro Ala Glu Pro Thr Gly
               260                 265                 270

Val Asn Met Leu Ser Pro Gly Glu Ser Glu His Leu Leu Glu Pro
               275                 280                 285

Ala Glu Ala Glu Arg Ser Gln Arg Arg Arg Leu Leu Val Pro Ala
               290                 295                 300

Asn Glu Gly Asp Pro Thr Glu Thr Leu Arg Gln Cys Phe Asp Asp
               305                 310                 315

Phe Ala Asp Leu Val Pro Phe Asp Ser Trp Glu Pro Leu Met Arg
               320                 325                 330

Lys Leu Gly Leu Met Asp Asn Glu Ile Lys Val Ala Lys Ala Glu
               335                 340                 345

Ala Ala Gly His Arg Asp Thr Leu Tyr Thr Met Leu Ile Lys Trp
               350                 355                 360
```

```
                                 -continued

Val Asn Lys Thr Gly Arg Asp Ala Ser Val His Thr Leu Leu Asp
                365                 370                 375

Ala Leu Glu Thr Leu Gly Glu Arg Leu Ala Lys Gln Lys Ile Glu
                380                 385                 390

Asp His Leu Leu Ser Ser Gly Lys Phe Met Tyr Leu Glu Gly Asn
                395                 400                 405

Ala Asp Ser Ala Xaa Ser
                410
```